United States Patent
Torgerson

(10) Patent No.: US 10,933,242 B2
(45) Date of Patent: Mar. 2, 2021

(54) THERAPY PARAMETER SELECTION BASED ON ECAP FEEDBACK

(71) Applicant: Medtronic, Inc., Minneapolis, MN (US)

(72) Inventor: Nathan A. Torgerson, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 532 days.

(21) Appl. No.: 15/720,848

(22) Filed: Sep. 29, 2017

(65) Prior Publication Data

US 2019/0099601 A1  Apr. 4, 2019

(51) Int. Cl.
*A61N 1/36* (2006.01)
*A61B 5/04* (2006.01)
(Continued)

(52) U.S. Cl.
CPC ...... *A61N 1/36067* (2013.01); *A61B 5/04001* (2013.01); *A61B 5/076* (2013.01); *A61B 5/12* (2013.01); *A61B 5/16* (2013.01); *A61B 5/486* (2013.01); *A61B 5/4836* (2013.01); *A61B 5/4848* (2013.01); *A61B 5/686* (2013.01);
(Continued)

(58) Field of Classification Search
CPC ............ A61N 1/36067; A61N 1/36062; A61N 1/36034; A61N 1/3606; A61N 1/36139; A61N 1/36146; A61N 1/36085; A61N 1/36107; A61N 1/3615; A61N 1/36164; G16H 20/30; A61B 5/076; A61B 5/12; A61B 5/16; A61B 5/4836; A61B 5/4848; A61B 5/486; A61B 5/686
See application file for complete search history.

(56) References Cited

U.S. PATENT DOCUMENTS 7,450,992 B1   11/2008  Cameron
2012/0257698 A1* 10/2012  Zhang ................. H03M 1/1265
                                              375/355
(Continued)

FOREIGN PATENT DOCUMENTS

WO        2012155188 A1    11/2012

OTHER PUBLICATIONS

International Search Report and Written Opinion of International Application No. PCT/US2018/041398, dated Sep. 19, 2018, 13 pp.
(Continued)

*Primary Examiner* — Catherine M Voorhees
*Assistant Examiner* — Roland Dinga
(74) *Attorney, Agent, or Firm* — Shumaker & Sieffert, P.A.

(57) ABSTRACT

Techniques for therapy delivery are described. A processing circuit may adjust a first therapy parameter from a first level to a second level, and responsive to the adjustment of the first therapy parameter, compare a level of an evoked compound action potential (ECAP) generated from therapy delivery based on the adjusted first therapy parameter to an ECAP threshold. The processing circuit may adjust a second therapy parameter from a third level to a fourth level based on the comparison. The second therapy parameter is different than the first therapy parameter. The processing circuit may cause therapy delivery with the first therapy parameter at the second level and the second therapy parameter at the fourth level.

44 Claims, 6 Drawing Sheets

(51) Int. Cl.
*A61B 5/07* (2006.01)
*A61B 5/00* (2006.01)
*A61B 5/16* (2006.01)
*G16H 20/30* (2018.01)
*A61B 5/12* (2006.01)

(52) U.S. Cl.
CPC ....... *A61N 1/3606* (2013.01); *A61N 1/36034* (2017.08); *A61N 1/36062* (2017.08); *A61N 1/36132* (2013.01); *A61N 1/36139* (2013.01); *A61N 1/36146* (2013.01); *G16H 20/30* (2018.01); *A61N 1/3615* (2013.01); *A61N 1/36085* (2013.01); *A61N 1/36107* (2013.01); *A61N 1/36164* (2013.01)

(56) References Cited

U.S. PATENT DOCUMENTS

| | | |
|---|---|---|
| 2014/0243926 A1 | 8/2014 | Carcieri |
| 2014/0277282 A1* | 9/2014 | Jaax ................... A61N 1/36139 607/59 |
| 2015/0032181 A1 | 1/2015 | Baynham et al. |
| 2015/0141857 A1* | 5/2015 | Nallathambi ........ A61B 5/0452 600/509 |
| 2016/0082262 A1 | 3/2016 | Parramon et al. |
| 2016/0121124 A1 | 5/2016 | Johanek et al. |
| 2016/0135705 A1* | 5/2016 | Liu .................... A61B 5/04012 600/509 |
| 2016/0157769 A1 | 6/2016 | Min et al. |
| 2016/0175592 A1 | 6/2016 | Smith et al. |
| 2016/0206883 A1 | 7/2016 | Bomzin et al. |
| 2016/0303376 A1* | 10/2016 | Dinsmoor ............ A61B 5/0488 |
| 2020/0023188 A1 | 1/2020 | Thacker et al. |
| 2020/0085330 A1* | 3/2020 | Di Poian .............. A61B 5/7232 |

OTHER PUBLICATIONS

"Strength Duration Curve [SDC]—Mobile Physiotherapy Clinic," accessed on Sep. 25, 2017, from http://mobilephysiotherapyclinic.in/strength-duration-curvesdc/, 11 pp.

Examination Report from counterpart Australian Application No. 2018341824, dated May 11, 2020, 4 pp.

Response to Examination Report dated May 11, 2020, from counterpart Australian Application No. 2018341824, filed Aug. 10, 2020, 3 pp.

Examination Report No. 2 from counterpart Australian Application No. 2018341824, dated Aug. 31, 2020, 3 pp.

* cited by examiner

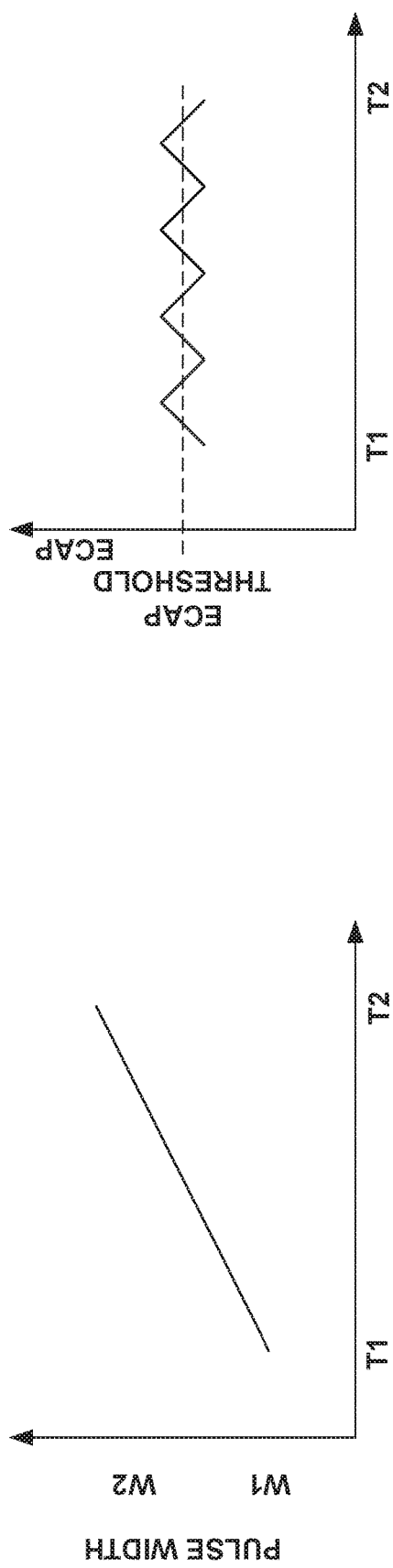
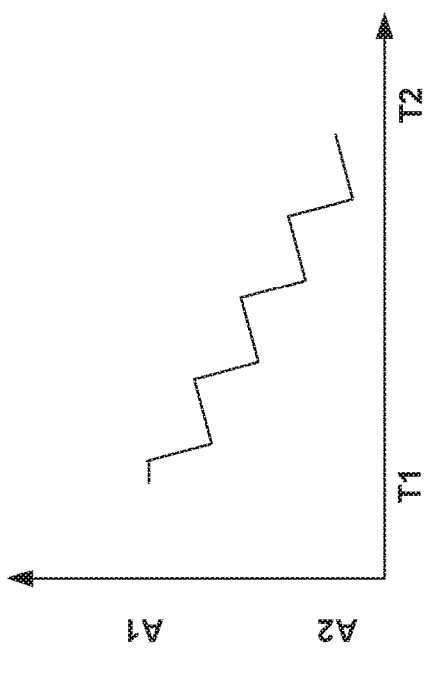
FIG. 3A
FIG. 3B
FIG. 3C

THERAPY PARAMETER SELECTION BASED ON ECAP FEEDBACK

TECHNICAL FIELD

This disclosure generally relates to electrical stimulation therapy.

BACKGROUND

Medical devices may be external or implanted, and may be used to deliver electrical stimulation therapy to patients via various tissue sites to treat a variety of symptoms or conditions such as chronic pain, tremor, Parkinson's disease, epilepsy, urinary or fecal incontinence, sexual dysfunction, obesity, or gastroparesis. A medical device may deliver electrical stimulation therapy via one or more leads that include electrodes located proximate to target locations associated with the brain, the spinal cord, pelvic nerves, peripheral nerves, or the gastrointestinal tract of a patient. Hence, electrical stimulation may be used in different therapeutic applications, such as deep brain stimulation (DBS), spinal cord stimulation (SCS), pelvic stimulation, gastric stimulation, or peripheral nerve field stimulation (PNFS).

A clinician may select values for a number of programmable parameters in order to define the electrical stimulation therapy to be delivered by the implantable stimulator to a patient. For example, the clinician may select one or more electrodes, a polarity of each selected electrode, a voltage or current amplitude, a pulse width, and a pulse frequency as stimulation parameters. A set of parameters, such as a set including electrode combination, electrode polarity, amplitude, pulse width and pulse rate, may be referred to as a program in the sense that they define the electrical stimulation therapy to be delivered to the patient.

SUMMARY

In some examples, the disclosure describes example medical devices, systems, and techniques for adjusting therapy parameters based on whether adjustment to different therapy parameters causes an evoked compound action potential (ECAP) to be greater than or less than an ECAP threshold. Over time, a patient may become accommodated to the therapy, impacting its effectiveness. To avoid accommodation, in the example techniques, a medical device may adjust the therapy parameters of the therapy that is delivered. However, adjustment of therapy parameters may also result in discomfort to the patient if the patient perceives changes in the intensity the therapy.

One way to determine intensity of the therapy is the level of the ECAP that is evoked in response to the delivery of therapy. For example, if the level of the ECAP is greater than an ECAP threshold, then the intensity may be too high, and if the level of the ECAP is less than the ECAP threshold, then the intensity may not be high enough. In the example techniques described in this disclosure, the medical device may adjust a first therapy parameter and, during or after adjustment, compare the level of the ECAP to the ECAP threshold. Based on the comparison, the medical device may adjust another therapy parameter to increase or decrease the level of the ECAP as appropriate. In this manner, by periodically or randomly adjusting a first therapy parameter, the patient may not experience accommodation, and by adjusting a second, different therapy parameter, the medical device may reduce the likelihood that the intensity of the therapy will cause discomfort.

In one example, this disclosure describes a method of therapy delivery, the method comprising adjusting a first therapy parameter from a first level to a second level different than the first level, responsive to the adjustment of the first therapy parameter, comparing a level of an evoked compound action potential (ECAP) generated in response to therapy delivered with the adjusted first therapy parameter to an ECAP threshold, adjusting a second therapy parameter from a third level to a fourth level different than the third level based on the comparison, wherein the second therapy parameter is different than the first therapy parameter, and causing delivery of the therapy with the first therapy parameter at the second level and the second therapy parameter at the fourth level.

In one example, this disclosure describes a device for therapy delivery, the device comprising a stimulation circuit and a processing circuit. The processing circuit is configured to adjust a first therapy parameter from a first level to a second level different than the first level, responsive to the adjustment of the first therapy parameter, compare a level of an evoked compound action potential (ECAP) generated in response to therapy delivered with the adjusted first therapy parameter to an ECAP threshold, adjust a second therapy parameter from a third level to a fourth level different than the third level based on the comparison, wherein the second therapy parameter is different than the first therapy parameter, and cause the stimulation circuit to deliver therapy with the first therapy parameter at the second level and the second therapy parameter at the fourth level.

In one example, the disclosure describes a computer-readable storage medium storing instructions thereon that when executed cause one or more processors of a device for therapy delivery to adjust a first therapy parameter from a first level to a second level different than the first level, responsive to the adjustment of the first therapy parameter, compare a level of an evoked compound action potential (ECAP) generated in response to therapy delivered with the adjusted first therapy parameter to an ECAP threshold, adjust a second therapy parameter from a third level to a fourth level different than the third level based on the comparison, wherein the second therapy parameter is different than the first therapy parameter, and cause delivery of the therapy with the first therapy parameter at the second level and the second therapy parameter at the fourth level.

In one example, the disclosure describes a device for therapy delivery, the device comprising means for adjusting a first therapy parameter from a first level to a second level different than the first level, responsive to the adjustment of the first therapy parameter, means for comparing a level of an evoked compound action potential (ECAP) generated in response to therapy delivered with the adjusted first therapy parameter to an ECAP threshold, means for adjusting a second therapy parameter from a third level to a fourth level different than the third level based on the comparison, wherein the second therapy parameter is different than the first therapy parameter, and means for causing delivery of the therapy with the first therapy parameter at the second level and the second therapy parameter at the fourth level.

In one example, the disclosure describes a system for therapy delivery, the system comprising an implantable medical device (IMD) comprising a stimulation circuit, one or more leads coupled to the IMD, and a processing circuit. The processing circuit is configured to adjust a first therapy parameter from a first level to a second level different than the first level, responsive to the adjustment of the first therapy parameter, compare a level of an evoked compound action potential (ECAP), sensed via at least one of the one or more leads, generated in response to therapy delivered with the adjusted first therapy parameter to an ECAP threshold, adjust a second therapy parameter from a third level to a fourth level different than the third level based on the comparison, wherein the second therapy parameter is different than the first therapy parameter, and cause the stimulation circuit to deliver therapy with the first therapy parameter at the second level and the second therapy parameter at the fourth level via at least one of the one or more leads.

The details of one or more examples of the techniques of this disclosure are set forth in the accompanying drawings and the description below. Other features, objects, and advantages of the techniques will be apparent from the description and drawings, and from the claims.

BRIEF DESCRIPTION OF DRAWINGS

FIGS. 3A-3C are timing diagrams illustrating an example operation for therapy adjustment according to the techniques of this disclosure.

DETAILED DESCRIPTION

Figure 1:
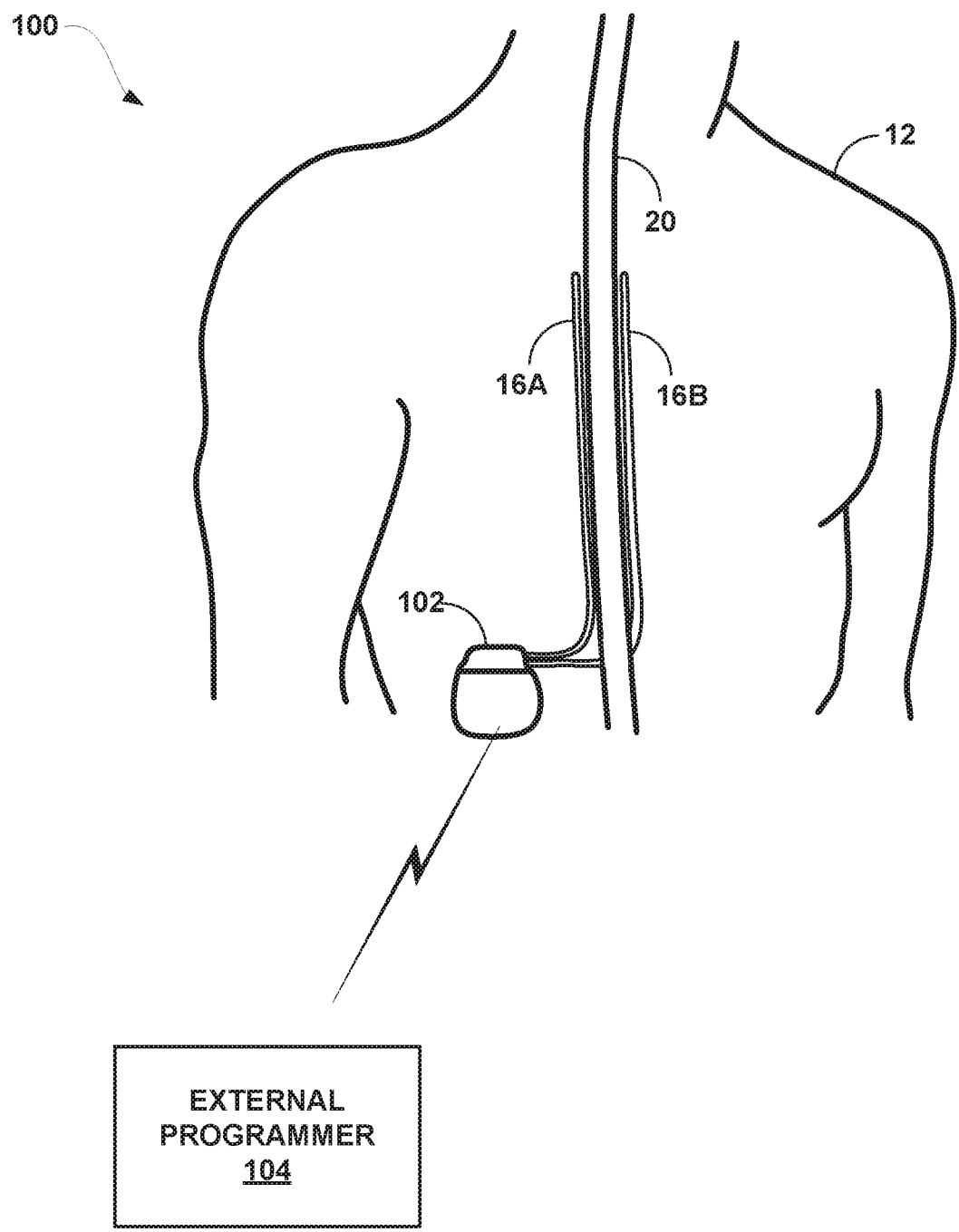
FIG. 1 is a conceptual diagram illustrating an example system that includes a medical device programmer and an implantable medical device (IMD) configured to deliver spinal cord stimulation (SCS) therapy according to the techniques of the disclosure.

In some examples, the disclosure describes example medical devices, systems, and techniques for automatically adjusting electrical stimulation therapy delivered to a patient to prevent or reduce the occurrence of evoked action potentials in tissue of the patient. For example, a medical device system may be configured to determine that electrical stimulation therapy being delivered to a patient according to a set of stimulation parameter values evokes an action potential in a tissue of a patient, e.g., by sensing the evoked compound action potentials in a tissue of the patient via one or more sensors, such as sense electrodes. Based on the determination, the medical device system may be configured to adjust one or more of the stimulation parameter values defining the electrical stimulation therapy delivered to the patient.

Adjusting various therapy parameters is one method to attempt to avoid or reduce accommodation, where due to the patient adapting to the therapy, the efficacy of the therapy may reduce. However, periodic therapy parameter adjustment or random therapy parameter adjustment may cause fluctuation in the intensity of the stimulation, resulting in patient discomfort. The intensity of stimulation monitored or measured using evoked compound action potentials (ECAPs). For instance, if the level of the ECAP is greater than an ECAP threshold, i.e., a level of the ECAP that corresponds to patient discomfort, the intensity of stimulation may be such that the patient feels discomfort, but if the level of the ECAP is less than the ECAP threshold, the intensity of stimulation may be such that the patient feels therapeutic benefits, without the discomfort. Level of the ECAP may be the peak or average level of the ECAP.

The example techniques relate to adjusting therapy parameters to avoid accommodation, while adjusting another therapy parameter based on sensed ECAPs to keep the intensity of stimulation such that the therapy may not cause discomfort. As an example, the medical device may adjust at least one of amplitude or pulse width until the sensed level of the ECAP is less than or equal to an ECAP threshold. The medical device may adjust a first therapy parameter (e.g., amplitude or pulse width) for one or more first pulses over a first period of time, sense the level of the ECAP in response to the first pulses, and based on the sensed ECAP, adjust a second therapy parameter (e.g., the other one of amplitude or pulse width) of one or more second pulses over a second period of time, e.g., to maintain the level of the sensed ECAP at less than or equal to the ECAP threshold. As another example, the level of the ECAP may be less than the ECAP threshold, and the medical device may adjust at least one of amplitude or pulse width, e.g., over a series of pulses, until the level of the sensed ECAP is approximately equal to the ECAP threshold. The medical device may adjust a first therapy parameter, and based on the level of the sensed ECAP, adjust a second therapy parameter, e.g., over a series of pulses, to increase the level of the ECAP until it is approximately equal to the ECAP threshold. In the examples described in this disclosure, the medical device may sense and adjust therapy on a pulse-by-pulse basis or every N pulses, or every N seconds.

The ECAP threshold need not necessarily be a constant threshold, but may instead be different for different levels of the therapy parameters. As an example, the ECAP threshold may be based on the amount by which the therapy parameter is adjusted. For example, if after adjusting the first therapy parameter, the second therapy parameter is adjusted from a first level, then the ECAP threshold may be at a first ECAP threshold. If, however, after adjusting the first therapy parameter, the second therapy parameter is adjusted from a second level, then the ECAP threshold may be at a second ECAP threshold.

FIG. 1 is a conceptual diagram illustrating example system 100 that includes implantable medical device (IMD) 102 configured to deliver electrical stimulation therapy to patient 12. In the example shown in FIG. 1, IMD 102 is configured to deliver spinal cord stimulation (SCS) therapy according to the techniques of the disclosure. Although the techniques described in this disclosure are generally applicable to a variety of medical devices including external and implantable medical devices (IMDs), application of such techniques to IMDs and, more particularly, implantable electrical stimulators (e.g., neurostimulators) will be described for purposes of illustration. More particularly, the disclosure will refer to an implantable spinal cord stimulation (SCS) system for purposes of illustration, but without limitation as to other types of medical devices or other therapeutic applications of medical devices.

As shown in FIG. 1, system 100 includes an IMD 102, leads 16A, 16B, and external programmer 104 shown in conjunction with a patient 12, who is ordinarily a human patient. In the example of FIG. 1, IMD 102 is an implantable electrical stimulator that is configured to generate and deliver electrical stimulation therapy to patient 12 via electrodes of leads 16A, 16B, e.g., for relief of chronic pain or other symptoms. IMD 102 may be a chronic electrical stimulator that remains implanted within patient 12 for weeks, months, or even years. In other examples, IMD 102 may be a temporary, or trial, stimulator used to screen or evaluate the efficacy of electrical stimulation for chronic therapy. In one example, IMD 102 is implanted within patient 12, while in another example, IMD 102 is an external device coupled to percutaneously implanted leads. In some examples, IMD uses one or more leads, while in other examples, IMD 102 is leadless.

IMD 102 may be constructed of any polymer, metal, or composite material sufficient to house the components of IMD 102 (e.g., components illustrated in FIG. 2) within patient 12. In this example, IMD 102 may be constructed with a biocompatible housing, such as titanium or stainless steel, or a polymeric material such as silicone, polyurethane, or a liquid crystal polymer, and surgically implanted at a site in patient 12 near the pelvis, abdomen, or buttocks. In other examples, IMD 102 may be implanted within other suitable sites within patient 12, which may depend, for example, on the target site within patient 12 for the delivery of electrical stimulation therapy. The outer housing of IMD 102 may be configured to provide a hermetic seal for components, such as a rechargeable or non-rechargeable power source. In addition, in some examples, the outer housing of IMD 102 may be selected from a material that facilitates receiving energy to charge the rechargeable power source.

Electrical stimulation energy, which may be constant current or constant voltage based pulses, for example, is delivered from IMD 102 to one or more target tissue sites of patient 12 via one or more electrodes (not shown) of implantable leads 16A and 16B (collectively "leads 16"). In the example of FIG. 1, leads 16 carry electrodes that are placed adjacent to the target tissue of spinal cord 20. One or more of the electrodes may be disposed at a distal tip of a lead 16 and/or at other positions at intermediate points along the lead. Leads 16 may be implanted and coupled to IMD 102. The electrodes may transfer electrical stimulation generated by an electrical stimulation circuit in IMD 102 to tissue of patient 12. Although leads 16 may each be a single lead, lead 16 may include a lead extension or other segments that may aid in implantation or positioning of lead 16. In some other examples, IMD 102 may be a leadless stimulator with one or more arrays of electrodes arranged on a housing of the stimulator rather than leads that extend from the housing. In addition, in some other examples, system 100 may include one lead or more than two leads, each coupled to IMD 102 and directed to similar or different target tissue sites.

The electrodes of leads 16 may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), or any other type of electrodes capable of forming unipolar, bipolar or multipolar electrode combinations for therapy. Ring electrodes arranged at different axial positions at the distal ends of lead 16 will be described for purposes of illustration.

The deployment of electrodes via leads 16 is described for purposes of illustration, but arrays of electrodes may be deployed in different ways. For example, a housing associated with a leadless stimulator may carry arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some examples, electrode arrays may include electrode segments, which may be arranged at respective positions around a periphery of a lead, e.g., arranged in the form of one or more segmented rings around a circumference of a cylindrical lead.

The therapy parameters for a therapy program (also referred to herein as a set of electrical stimulation parameter values) that controls delivery of stimulation therapy by IMD 102 through the electrodes of leads 16 may include information identifying which electrodes have been selected for delivery of stimulation according to a stimulation program, the polarities of the selected electrodes, i.e., the electrode combination for the program, and voltage or current amplitude, pulse rate, and pulse width of stimulation delivered by the electrodes. Delivery of stimulation pulses will be described for purposes of illustration.

Although FIG. 1 is directed to SCS therapy, e.g., used to treat pain, in other examples system 100 may be configured to treat any other condition that may benefit from electrical stimulation therapy. For example, system 100 may be used to treat tremor, Parkinson's disease, epilepsy, a pelvic floor disorder (e.g., urinary incontinence or other bladder dysfunction, fecal incontinence, pelvic pain, bowel dysfunction, or sexual dysfunction), obesity, gastroparesis, or psychiatric disorders (e.g., depression, mania, obsessive compulsive disorder, anxiety disorders, and the like). In this manner, system 100 may be configured to provide therapy taking the form of deep brain stimulation (DB S), peripheral nerve stimulation (PNS), peripheral nerve field stimulation (PNFS), cortical stimulation (CS), pelvic floor stimulation, gastrointestinal stimulation, or any other stimulation therapy capable of treating a condition of patient 12.

In some examples, lead 16 may include one or more sensors configured to allow IMD 102 to monitor one or more parameters of patient 12. The one or more sensors may be provided in addition to, or in place of, therapy delivery by lead 16.

IMD 102 is configured to deliver electrical stimulation therapy to patient 12 via selected combinations of electrodes carried by one or both of leads 16, alone or in combination with an electrode carried by or defined by an outer housing of IMD 102. The target tissue for the electrical stimulation therapy may be any tissue affected by electrical stimulation, which may be in the form of electrical stimulation pulses or continuous waveforms. In some examples, the target tissue includes nerves, smooth muscle or skeletal muscle. In the example illustrated by FIG. 1, the target tissue is tissue proximate spinal cord 20, such as within an intrathecal space or epidural space of spinal cord 20, or, in some examples, adjacent nerves that branch off of spinal cord 20. Leads 16 may be introduced into spinal cord 20 in via any suitable region, such as the thoracic, cervical or lumbar regions. Stimulation of spinal cord 20 may, for example, prevent pain signals from traveling through spinal cord 20 and to the brain of patient 12. Patient 12 may perceive the interruption of pain signals as a reduction in pain and, therefore, efficacious therapy results.

IMD 102 generates and delivers electrical stimulation therapy to a target stimulation site within patient 12 via the electrodes of leads 16 to patient 12 according to one or more therapy programs. A therapy program defines values for one or more parameters that define an aspect of the therapy delivered by IMD 102 according to that program. For example, a therapy program that controls delivery of stimulation by IMD 102 in the form of pulses may define values for voltage or current pulse amplitude, pulse width, and pulse rate for stimulation pulses delivered by IMD 102 according to that program.

Moreover, in some examples, IMD 102 delivers electrical stimulation therapy to patient 12 according to multiple therapy programs, which may be stored as a therapy program group. For example, as described below, in some examples, IMD 102 may deliver different pulses of electrical stimulation signal via respective electrode combinations, and each of the electrode combinations may be associated with a respective therapy program. The therapy programs may be stored as a group, such that when IMD 102 generates and delivers electrical stimulation therapy via a selected group, IMD 102 delivers electrical stimulation signal via two or more therapy programs.

A user, such as a clinician or patient 12, may interact with a user interface of an external programmer 104 to program IMD 102. Programming of IMD 102 may refer generally to the generation and transfer of commands, programs, or other information to control the operation of IMD 102. In this manner, IMD 102 may receive the transferred commands and programs from programmer 104 to control stimulation therapy. For example, external programmer 104 may transmit therapy programs, stimulation parameter adjustments, therapy program selections, therapy program group selections, user input, or other information to control the operation of IMD 102, e.g., by wireless telemetry or wired connection.

In some cases, external programmer 104 may be characterized as a physician or clinician programmer if it is primarily intended for use by a physician or clinician. In other cases, external programmer 104 may be characterized as a patient programmer if it is primarily intended for use by a patient. A patient programmer may be generally accessible to patient 12 and, in many cases, may be a portable device that may accompany patient 12 throughout the patient's daily routine. For example, a patient programmer may receive input from patient 12 when the patient wishes to terminate or change stimulation therapy. In general, a physician or clinician programmer may support selection and generation of programs by a clinician for use by IMD 102, whereas a patient programmer may support adjustment and selection of such programs by a patient during ordinary use. In other examples, external programmer 104 may include, or be part of, an external charging device that recharges a power source of IMD 102. In this manner, a user may program and charge IMD 102 using one device, or multiple devices.

As described herein, information may be transmitted between external programmer 104 and IMD 102. Therefore, IMD 102 and programmer 104 may communicate via wireless communication using any techniques known in the art. Examples of communication techniques may include, for example, radiofrequency (RF) telemetry and inductive coupling, but other techniques are also contemplated. In some examples, programmer 104 may include a communication head that may be placed proximate to the patient's body near the IMD 102 implant site in order to improve the quality or security of communication between IMD 102 and programmer 104. Communication between programmer 104 and IMD 102 may occur during power transmission or separate from power transmission.

In some examples, IMD 102, in response to commands from external programmer 104, delivers electrical stimulation therapy according to a plurality of electrical stimulation therapy programs to a target tissue site of the spinal column 20 of patient 12 via electrodes (not depicted) on leads 16. In some examples, IMD 102 may modify therapy parameters of the therapy delivered to patient 12 so as to reduce patient accommodation, as one non-limiting example. For instance, IMD 102 may adjust a first therapy parameter from a first level to a second level after a set amount of time elapsed (e.g., periodically or randomly).

The adjustment of the first therapy parameter may ensure or increase the likelihood that patient 12 does not become accommodated to the therapy. When patient 12 receives the same therapy for an extended period of time, patient 12 may become accustomed to the paresthesia from the therapy, which may over time reduce efficacy of the therapy. Accordingly, by adjusting the first therapy parameter, the feeling of paresthesia may be kept because there will be some change to the amount or type of paresthesia that is felt.

However, it may be desirable to maintain the intensity of the therapy such that adjustment of the first therapy parameter does not cause the intensity to increase too much to a point where the paresthesia is uncomfortable for the patient. In this disclosure, intensity of the therapy may be indicated by an amount of an action potential that is evoked, which is referred to as an evoked compound action potential (ECAP). Therapy delivery encompasses a therapy volume within patient 12, and can cause neurons within the volume to evoke an action potential that travels up and down spinal cord 20. The amount of action potentials (e.g., number of action potential signals, or level of ECAP) that are evoked may be based on the various therapy parameters such as amplitude, pulse width, frequency, etc.

In some examples, adjusting the first therapy parameter may cause the level of the ECAP to become too high (e.g., greater than an ECAP threshold). The level of the ECAP may be the average over multiple ECAPs within a time period following or coincident with stimulation delivery, or may be the peak level of the ECPA. IMD 102 may also adjust a second, different therapy parameter to ensure that the ECAP stays below the ECAP threshold, and in some cases, approximately equal to the ECAP threshold. In some examples, adjusting the first therapy parameter of the stimulation may cause the ECAP to become too low (e.g., less than the ECAP threshold, which may mean less efficacious therapy). Accordingly, IMD 102 may adjust the second, different therapy parameter of the stimulation to ensure that the ECAP is approximately equal to the ECAP threshold.

In some examples, the ECAP threshold is not a threshold where patient 12 first begins to experience paresthesia. The threshold could possibly be the level where patient 12 first feels stimulation, but it is also possible that the ECAP threshold is at a level low enough where patient 12 does not feel the stimulation yet. For instance, the action potential is present near the stimulating electrode but the compound action potential is not strong enough to be sensed by the body.

The ECAP threshold may be a non-zero numerical value indicative of where patient 12 begins to experience paresthesia that is uncomfortable. For example, during a clinician visit, a clinician may modify a first therapy parameter of the stimulation pulses. Then, the clinician may modify a second, different therapy parameter of the stimulation pulses until the paresthesia that patient 12 begins to experience is uncomfortable. The clinician may note the ECAP level (e.g., as measured by IMD 102) when patient 12 indicated that the paresthesia is uncomfortable. This ECAP level at which paresthesia becomes uncomfortable may become the ECAP threshold.

The ECAP threshold may not be the same for all combination of therapy parameters. For instance, the ECAP threshold may be based on the level of the second therapy parameter, the rate at which the first therapy parameter is being adjusted, the starting level of the first and second therapy parameters, etc. As an example, if the first therapy parameter is a 60 microsecond pulse width and is increased to 100 microsecond pulse width, and then second therapy parameter is adjusted starting from 10 milliamps, patent 12 may indicate uncomfortable paresthesia when the level of the ECAP is measured at 50 microvolts. However, if the first therapy parameter is 100 microsecond pulse width and is increased to 500 microsecond pulse width, and then second therapy parameter is adjusted starting from 5 millamps, patent 12 may indicate uncomfortable paresthesia when the level of the ECAP is measured at 20 microvolts. Therefore, IMD 102 may set the ECAP threshold to which the ECAP is compared to different numerical values based on various factors.

For the adjustment, after adjusting the first therapy parameter, IMD 102 may deliver a stimulation pulse having the adjusted first therapy parameter, and IMD 102 may determine whether the level of the ECAP is greater than or less than the ECAP threshold (e.g., in response to the stimulation pulse). In some examples, the level of the ECAP may be an average or peak level of the ECAPs over a plurality of stimulation pulses. If IMD 102 determines that the ECAP is greater than the ECAP threshold, IMD 102 may adjust the second therapy parameter downwards to decrease the level of the ECAP until the level of the ECAP is less than or equal to the ECAP threshold. If IMD 102 determines that the level of the ECAP is less than the ECAP threshold, IMD 102 may adjust the second therapy parameter upwards to increase the level of the ECAP until the level of the ECAP is approximately equal to the ECAP threshold (e.g., within 10% of the ECAP threshold).

In some examples, the target tissue is a tissue of the spinal column 20 of patient 12. As one example, the target tissue may be a tissue of a dorsal column of the spinal column 20 of patient 12. In other examples, the target tissue is another nerve tissue of patient 12 or a muscle tissue of patient 12.

As described, the example techniques are based on determining the level of the ECAP for comparison to an ECAP threshold and adjustment of therapy parameters. During delivery of electrical stimulation therapy defined by one or more electrical stimulation programs, IMD 102, via the electrodes interposed on leads 16, senses target tissue site of the spinal column 20 of patient 12 to measure the electrical activity of the target tissue site. IMD 102 senses when electrical stimulation therapy defined by the one or more electrical stimulation programs evokes a compound action potential in the target tissue site of patient 12, e.g., with sense electrodes on one or more leads 16 and associated sense circuitry. In some examples, IMD 102 receives a signal indicative of the compound action potential from one or more sensors, e.g., one or more electrodes and circuitry, internal or external to patient 12. Such an example signal may include a signal indicating an electrically-evoked compound action potential (ECAP) of the tissue of the patient 12. Examples of the one or more sensors include one or more sensors configured to measure a compound action potential of the patient 12, or a physiological effect indicative of a compound action potential. For example, to measure a physiological effect of a compound action potential, the one or more sensors may be an accelerometer, a pressure sensor, a bending sensor, a sensor configured to detect a posture of patient 12, or a sensor configured to detect a respiratory function of patient 12. However, in other examples, external programmer 104 receives a signal indicating a compound action potential in the target tissue of patient 12 and transmits a notification to IMD 102.

In the example of FIG. 1, IMD 102 described as performing a plurality of processing and computing functions. However, external programmer 104 instead may perform one, several, or all of these functions. In this alternative example, IMD 102 functions to relay sensed signals to external programmer 104 for analysis, and external programmer 104 transmits instructions to IMD 102 to adjust the one or more parameters defining the electrical stimulation therapy based on analysis of the sensed signals. For example, IMD 102 may relay the sensed signal indicative of an ECAP to external programmer 104. External programmer 104 may compare the level of the ECAP to the ECAP threshold, and in response to the comparison, external programmer 104 may instruct IMD 102 to adjust another therapy parameter that defines the electrical stimulation therapy delivered to patient 12.

In general, spinal cord stimulation may become less effective over time for controlling chronic pain. One conventional techniques is to routinely attempt, by clinicians, to change the therapy parameters (e.g., amplitude, pulse width, and rate) to try to recapture pain control. This is usually done in the clinic, as the new settings may need to be titrated by the clinician for patient comfort.

However, in the example techniques described in this disclosure, the ECAP thresholds may be initially set at the clinic, but may be set at home as well by patient 12. Once the ECAP thresholds are set, the example techniques allow for automatic adjustment of therapy parameters without causing the intensity of the stimulation to fluctuate (e.g., therapy parameters are adjusted to avoid accommodation, but the ECAP is approximately equal to the ECAP threshold to avoid patient discomfort). The ability to change the settings may also allow the therapy to have long term efficacy, with the ability to keep the intensity of the stimulation (e.g., as indicated by the ECAP) consistent by comparing the sensed ECAP level to the ECAP threshold, allowing such adjustments to happen on a routine basis without the need for clinician or patient intervention.

By changing parameters automatically outside of the clinic, e.g., at home, in a way that is safe for patient 12 and may go unnoticed, IMD 102 may keep the stimulation new or varied with patient 12 and prevent accommodation of the therapy. For example, because the sensed ECAP level generated from the therapy is kept approximately equal to the ECAP threshold, patient 12 may not experience discomfort but at the same time is unable to accommodate the therapy.

Figure 2:
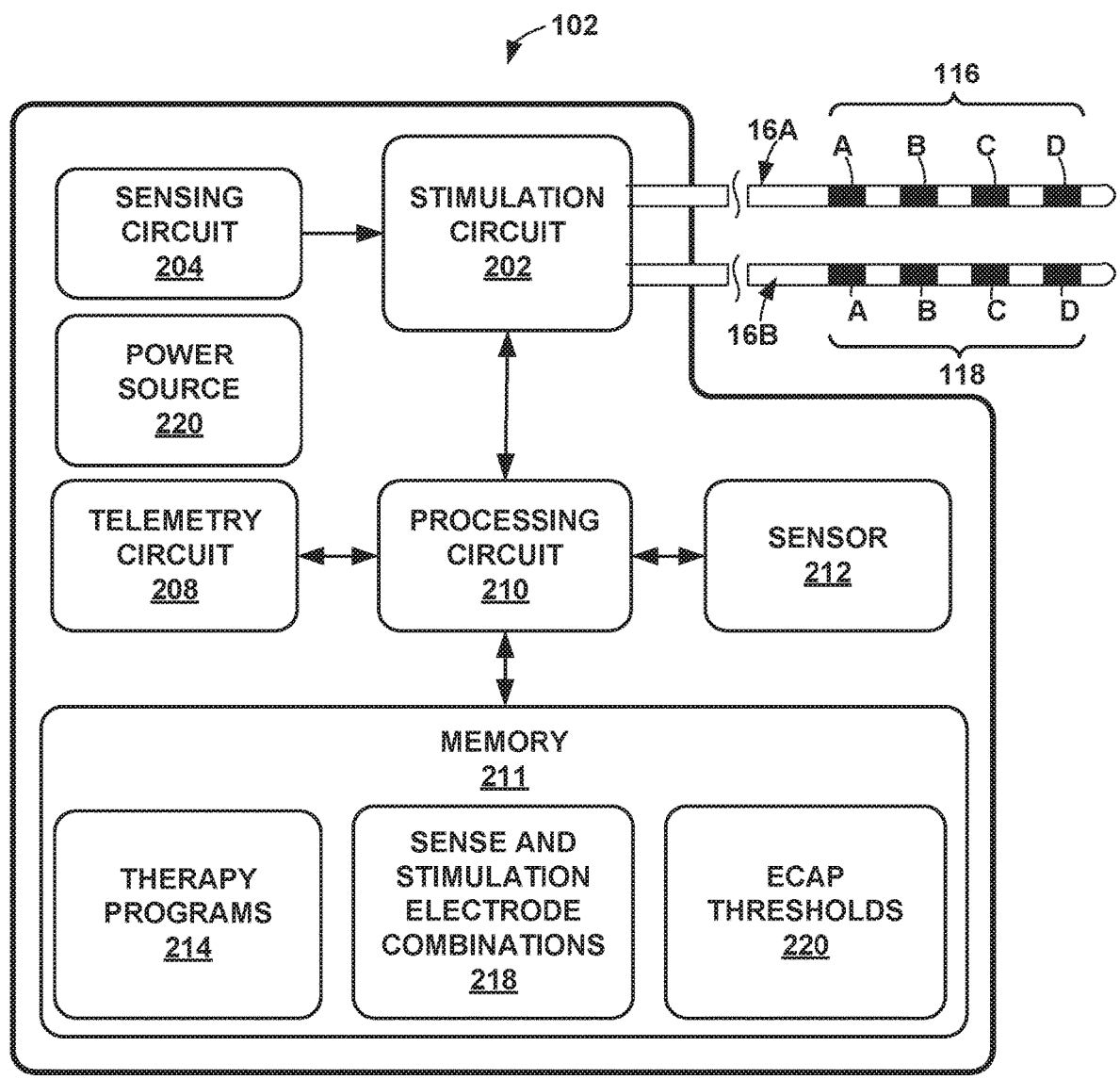
FIG. 2 is a block diagram of the example IMD of FIG. 1.

FIG. 2 is a block diagram of the example IMD 102 of FIG. 1. In the example shown in FIG. 2, IMD 102 includes processing circuit 210, memory 211, stimulation circuit 202, sensing circuit 204, telemetry circuit 208, sensor 212, and power source 220. Each of these circuits may be or include programmable or fixed function circuitry configured to perform the functions attributed to each respective circuit. For example, processing circuit 210 may include fixed-function or programmable circuitry, stimulation circuit 202 may include switch circuitry, sensing circuit 204 may include sensing circuitry for sensing signals, and telemetry circuit 208 may include telemetry circuitry for transmission and reception of signals. Memory 211 may include any volatile or non-volatile media, such as a random access memory (RAM), read only memory (ROM), non-volatile RAM (NVRAM), electrically erasable programmable ROM (EEPROM), flash memory, and the like. Memory 211 may store computer-readable instructions that, when executed by processing circuit 210, cause IMD 102 to perform various functions. Memory 211 may be a storage device or other non-transitory medium.

In the example shown in FIG. 2, memory 211 stores therapy programs 214 and sense electrode combinations and associated stimulation electrode combinations 218 in separate memories within memory 211 or separate areas within memory 211. Each stored therapy program 214 defines a particular set of electrical stimulation parameters (e.g., a therapy parameter set), such as a stimulation electrode combination, electrode polarity, current or voltage amplitude, pulse width, and pulse rate. In some examples, individual therapy programs may be stored as a therapy group, which defines a set of therapy programs with which stimulation may be generated. The stimulation signals defined by the therapy programs of the therapy group include stimulation pulses that may be delivered together on an overlapping or non-overlapping (e.g., time-interleaved) basis.

Accordingly, in some examples, stimulation circuit 202 generates electrical stimulation signals in accordance with the electrical stimulation parameters noted above. Other ranges of therapy parameter values may also be useful, and may depend on the target stimulation site within patient 12. While stimulation pulses are described, stimulation signals may be of any form, such as continuous-time signals (e.g., sine waves) or the like.

Processing circuit 210 may include any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processing circuit 210 herein may be embodied as firmware, hardware, software or any combination thereof. Processing circuit 210 controls stimulation circuit 202 according to therapy programs 214 stored in memory 211 to apply particular stimulation parameter values specified by one or more of programs, such as amplitude, pulse width, and pulse rate.

In the example shown in FIG. 2, the set of electrodes 116 includes electrodes 116A, 116B, 116C, and 116D, and the set of electrodes 118 includes electrodes 118A, 118B, 118C, and 118D. Processing circuit 210 also controls stimulation circuit 202 to generate and apply the stimulation signals to selected combinations of electrodes 116, 118. In some examples, stimulation circuit 202 includes a switch circuit that couples stimulation signals to selected conductors within leads 16, which, in turn, deliver the stimulation signals across selected electrodes 116, 118. Such a switch circuit may be a switch array, switch matrix, multiplexer, or any other type of switching circuit configured to selectively couple stimulation energy to selected electrodes 116, 118 and to selectively sense bioelectrical neural signals of spine 20 with selected electrodes 116, 118.

In other examples, however, stimulation circuit 202 does not include a switch circuit. In these examples, stimulation circuit 202 comprises a plurality of pairs of voltage sources, current sources, voltage sinks, or current sinks connected to each of electrodes 116, 118 such that each pair of electrodes has a unique signal circuit. In other words, in these examples, each of electrodes 116, 118 is independently controlled via its own signal circuit (e.g., via a combination of a regulated voltage source and sink or regulated current source and sink), as opposed to switching signals between electrodes 116, 118.

Stimulation circuit 202 may be a single channel or multi-channel stimulation circuit. In particular, stimulation circuit 202 may be capable of delivering a single stimulation pulse or multiple stimulation pulses at a given time via a single electrode combination or multiple stimulation pulses at a given time via multiple electrode combinations. In some examples, however, stimulation circuit 202 may be configured to deliver multiple channels on a time-interleaved basis. For example, a switch circuit of stimulation circuit 202 may serve to time divide the output of stimulation circuit 202 across different electrode combinations at different times to deliver multiple programs or channels of stimulation energy to patient 12. In another example, the stimulation circuit 202 may control the independent sources or sinks on a time-interleaved basis Electrodes 116, 118 on respective leads 16 may be constructed of a variety of different designs. For example, one or both of leads 16 may include two or more electrodes at each longitudinal location along the length of the lead, such as multiple electrodes at different perimeter locations around the perimeter of the lead at each of the locations A, B, C, and D. In one example, the electrodes may be electrically coupled to stimulation circuit 202, e.g., switching circuitry of the stimulation circuit 202, via respective wires that are straight or coiled within the housing of the lead and run to a connector at the proximal end of the lead. In another example, each of the electrodes of the lead may be electrodes deposited on a thin film. The thin film may include an electrically conductive trace for each electrode that runs the length of the thin film to a proximal end connector. The thin film may then be wrapped (e.g., a helical wrap) around an internal member to form the lead 16. These and other constructions may be used to create a lead with a complex electrode geometry.

Although sensing circuit 204 is incorporated into a common housing with stimulation circuit 202 and processing circuit 210 in FIG. 2, in other examples, sensing circuit 204 may be in a separate housing from IMD 102 and may communicate with processing circuit 210 via wired or wireless communication techniques.

In some examples, one or more of electrodes 116 and 118 may be suitable for sensing the ECAPs. For instance, electrodes 116 and 118 may sense the voltage of the ECAPs, where the sensed voltage indicates the level of the ECAP.

Sensor 212 may include one or more sensing elements that sense values of a respective patient parameter. As described, electrodes 116 and 118 may be the electrodes that sense the level of the ECAP. However, sensor 212 may use physiological levels to indirectly determine the level of the ECAP. For example, sensor 212 may include one or more accelerometers, optical sensors, chemical sensors, temperature sensors, pressure sensors, or any other types of sensors. Sensor 212 may output patient parameter values that may be used as feedback to control delivery of therapy. IMD 102 may include additional sensors within the housing of IMD 102 and/or coupled via one of leads 16 or other leads. In addition, IMD 102 may receive sensor signals wirelessly from remote sensors via telemetry circuit 208, for example. In some examples, one or more of these remote sensors may be external to patient (e.g., carried on the external surface of the skin, attached to clothing, or otherwise positioned external to the patient).

Telemetry circuit 208 supports wireless communication between IMD 102 and an external programmer 104 or another computing device under the control of processing circuit 210. Processing circuit 210 of IMD 102 may receive, as updates to programs, values for various stimulation parameters such as amplitude and electrode combination, from programmer 104 via telemetry circuit 208. The updates to the therapy programs may be stored within therapy programs 214 portion of memory 211. Telemetry circuit 208 in IMD 102, as well as telemetry circuits in other devices and systems described herein, such as programmer 104, may accomplish communication by radiofrequency (RF) communication techniques. In addition, telemetry circuit 208 may communicate with external medical device programmer 104 via proximal inductive interaction of IMD 102 with programmer 104. Accordingly, telemetry circuit 208 may send information to external programmer 104 on a continuous basis, at periodic intervals, or upon request from IMD 102 or programmer 104.

Power source 220 delivers operating power to various components of IMD 102. Power source 220 may include a small rechargeable or non-rechargeable battery and a power generation circuit to produce the operating power. Recharging may be accomplished through proximal inductive interaction between an external charger and an inductive charging coil within IMD 220. In some examples, power requirements may be small enough to allow IMD 220 to utilize patient motion and implement a kinetic energy-scavenging device to trickle charge a rechargeable battery. In other examples, traditional batteries may be used for a limited period of time.

According to the techniques of the disclosure, processing circuit 210 of IMD 102 receives, via telemetry circuit 208, instructions to deliver electrical stimulation therapy according to the one or more electrical stimulation therapy programs to a target tissue site of the spinal column 20 of patient 12 via a plurality of electrode combinations of electrodes 116, 118 of leads 16 and/or a housing of IMD 102. After a set amount of time (e.g., periodic, random, or triggered by a sensing input such as a change in poser or detection of patient 12 becoming more or less active), processing circuit 210 may adjust a first therapy parameter of the electrical stimulation therapy and cause stimulation circuit 202 to deliver therapy based on the adjusted first therapy parameter. Processing circuit 210 may receive, via an electrical signal sensed by sensing circuit 204, information indicative of an ECAP (e.g., a numerical value indicating the ECAP in electrical units such as voltage or power) produced in response to the stimulation. Processing circuit 210 may compare the level of the sensed ECAP to an ECAP threshold stored in ECAP thresholds 220 or an ECAP threshold determined in some other way such as by dynamically setting the ECAP threshold. Based on the comparison, processing circuit 210 may adjust a second, different therapy parameter. The adjustment may be a function of the comparison. For example, if the sensed ECAP level exceeds the ECAP threshold, the amplitude, pulse width or pulse rate of the stimulation may be adjusted downward. Alternatively, if the sensed ECAP level is less than the ECAP threshold, then the pulse width or pulse rate of the stimulation may be adjusted upward.

In one example, the electrical stimulation signal comprises of one or more electrical pulses (e.g., a pulse train), wherein each pulse has a pulse width in a range of about 2 microseconds to about 100 microseconds. In a further example, each pulse has a pulse width in a range of about 20 microseconds to about 60 microseconds. In one example, the electrical stimulation signal comprises pulses having a pulse width in a range of about 30 microseconds to about 60 microseconds. In one example, the electrical stimulation signal comprises pulses having a pulse width of approximately 50 microseconds. In one example, the electrical stimulation signal comprises pulses having a pulse width of approximately 60 microseconds. In one example, the electrical stimulation signal comprises pulses having a first amplitude and a first pulse width (e.g., 100 microseconds), and pulses having a second amplitude greater than the first amplitude based on the sensed level of the ECAP.

In some examples, IMD 102 delivers the pulses of the electrical stimulation signal via different electrode combinations of two or more of electrodes 116A-116D and 118A-118D and a housing of IMD 102. For example, IMD 102 may alternate delivery of pulses between two or more different electrode combinations, or may otherwise interleave the pulses using two or more electrode combinations in any suitable order. In one example, each electrode combination comprises at least one electrode functioning as an anode and at least one other electrode functioning as a cathode, and these electrodes are unique to the electrode combination in that the same electrodes are not used in other electrode combinations that are used to delivery time-interleaved stimulation pulses.

In some examples, the electrical stimulation therapy signal may have a frequency range of approximately 50-500 Hertz, and generally around 400 Hertz. However, in other examples, the electrical stimulation therapy has a frequency greater than approximately 1 Hertz in some examples, greater than 1,200 Hertz in some examples, greater than 1,500 Hertz in other examples, greater than 5,000 Hertz in other examples, or greater than 10,000 Hertz in still other examples. When higher frequencies are used in a system using sensed ECAP levels to determine therapy, it may be useful to briefly suspend the delivery of electrical stimulation and deliver a single pulse at a lower amplitude (or a burst of pulses having a lower frequency) to detect the presence of ECAP.

During delivery of electrical stimulation therapy according to the one or more electrical stimulation programs, processing circuit 210, via electrodes 116, 118 interposed along leads 16, senses the target tissue site of the spinal column 20 of patient 12 and measures the electrical activity of the target tissue site. For example, electrodes 116, 118 may sense a level of the ECAP of the tissue of the patient. Upon determining the level of the ECAP, processing circuit 210 may compare the level of the sensed ECAP to an ECAP threshold for adjustment of another therapy parameter (e.g., the processing circuit may adjust at least one electrical stimulation therapy program of the plurality of electrical stimulation therapy programs).

In an alternative example, processing circuit 210 receives a signal indicative of a level of a sensed ECAP from one or more sensors internal or external to patient 12. Upon receiving the signal, processing circuit 210 adjusts at least one electrical stimulation therapy program of the plurality of electrical stimulation therapy programs. Examples of the one or more sensors include one or more sensors configured to measure a compound action potential of the patient 12, or a side effect indicative of a compound action potential. For example, the one or more sensors may be electrodes 116 or 118, or ECAP may be sensed indirectly with an accelerometer, a pressure sensor, a bending sensor, a sensor configured to detect a posture of patient 12, or a sensor configured to detect a respiratory function of patient 12. However, in other examples, rather than processing circuit 210, external programmer 104 receives a signal indicating a level of a sensed ECAP in the target tissue of patient 12 and transmits the signal to processing circuit 210. Processing circuit 210 receives the signal via telemetry circuit 208.

As described above, over time, patient 12 may become accustomed to therapy. In some examples, IMD 102 may include an internal timer, and after a set amount of time is elapsed, processing circuit 210 may adjust a therapy parameter of the therapy that is being delivered. In some examples, rather than relying on an internal timer, processing circuit 210 may be configured to randomly adjust the therapy parameter. As an example, processing circuit 210 may change (e.g., increase or decrease) the pulse width by 100 microseconds once every 24 hours.

The change in the therapy parameter may potentially change the intensity of the therapy. Intensity of the therapy is a measure of the level of ECAP that is evoked from the delivery of therapy. If the level of the ECAP is too high, the patient may experience paresthesia or other sensations that are uncomfortable or otherwise undesirable. A level of ECAP that is too low may indicate that the patient may not experience sufficiently efficacious therapy. Therefore, processing circuit 210 may adjust a first therapy parameter from a first level to a second level, and responsive to the adjustment of the first therapy parameter, compare a sensed level of an ECAP generated from therapy delivery based on the adjusted first therapy parameter to an ECAP threshold. Processing circuit 210 may adjust a second, different therapy parameter from a third level to a fourth level based on the comparison, and cause stimulation circuit 204 to deliver therapy with the first therapy parameter at the second level and the second therapy parameter at the fourth level. Processing circuit 210 may then determine whether an additional amount of time elapsed (or at some random time), and then repeat these operations (e.g., by adjusting first or second therapy parameter, and adjusting the other one of the first or second therapy parameter based on comparison of the level of the ECAP to the ECAP threshold).

As an example, processing circuit 210 may determine that the level of the ECAP is greater than the ECAP threshold based on the comparison. In this example, responsive to determining that the level of the ECAP is greater than the ECAP threshold, processing circuit 210 may adjust the second therapy parameter from the third level to the fourth level. In this example, the level of the ECAP is less than or equal to the ECAP threshold when the therapy is delivered with the second therapy parameter at the fourth level.

As another example, processing circuit 210 may determine that the level of the ECAP is less than or equal to the ECAP threshold based on the comparison. In this example, responsive to determining that the level of the ECAP is less than or equal to the ECAP threshold, processing circuit 210 may adjust the second therapy parameter from the third level to the fourth level. In this example, the level of the ECAP is approximately equal to the ECAP threshold when the therapy is delivered with the second therapy parameter at the fourth level.

In some examples, processing circuit 210 may be configured to automatically adjust the second therapy parameter whenever the first therapy parameter is adjusted regardless of the level of the ECAP. For instance, memory 211 may store a therapy table with information that indicates generally what the level for the second therapy parameter should be for a given level of the first therapy parameter. However, if processing circuit 210 only relied on the table to set the level of the second therapy parameter, it may be possible that therapy is not sufficiently intense.

Accordingly, in some examples, processing circuit 210, responsive to adjusting the first therapy parameter, may adjust the second therapy parameter from one value to another value based on the therapy table. In such examples, processing circuit 210 may further adjust the second therapy parameter from its adjusted value based on the comparison of the level of the ECAP to the ECAP threshold.

Processing circuit 210 may adjust the first therapy parameter at different rates. As one example, processing circuit 210 may gradually adjust the first therapy parameter. As another example, processing circuit 210 may quickly adjust the first therapy parameter. As an example, the first therapy parameter may be pulse width, and processing circuit 210 may adjust the pulse width from 60 microseconds to 1000 microseconds over 30 seconds in 10 microsecond steps. This is an example of gradually adjusting the first therapy parameter. As another example, processing circuit 210 may adjust the pulse width from 60 microseconds to 1000 microseconds over 5 seconds, which is an example of quickly adjusting the first therapy parameter. In other example, rather than pulse width, the first therapy parameter may be amplitude that processing circuit 210 gradually or quickly changes.

The ECAP threshold may be constant in some examples. However, changing the ECAP threshold may be another way in which to ensure that patient 12 does not become accommodated to the therapy. In some examples, the ECAP threshold may be selected based on the therapy characteristics.

ECAP thresholds 220 may store a plurality of ECAP thresholds, and processing circuit 210 may select an appropriate threshold. As one example, during clinic visit, the clinician may adjust a first therapy parameter from a first level to a second level. The clinician may then set an ECAP threshold, and processing circuit 210 may adjust the second therapy parameter such that the delivery of therapy causes patient 12 to generate a level of ECAP that is approximately equal to the set ECAP threshold. Patient 12 may indicate to a clinician, or via user input into a programmer such as a patient programmer, whether he/she is experiencing discomfort. The clinician and/or the programmer may then adjust the ECAP threshold, which causes processing circuit 210 to readjust the second therapy parameter, and patient 12 may indicate whether he/she is experiencing discomfort. The clinician may repeat these steps until patient 12 indicates discomfort. For the given first therapy parameter and the starting level (e.g., first level) and final level (e.g., second level), the clinician may store the ECAP threshold that caused discomfort in ECAP threshold 220. The clinician may repeat these operations for different starting levels for the first therapy parameter, different final levels for the first therapy parameter, and different rates of adjustment of the first therapy parameter, and store the different ECAP thresholds in ECAP thresholds 220.

As an illustrative example, the clinician may set the pulse width of the stimulation at 60 us, and may increase the ECAP threshold starting from 50 microvolts. As the clinician is increasing the ECAP threshold, processing circuit 210 may adjust the pulse amplitude of the stimulation so that the ECAP that is generated is approximately equal to the ECAP threshold. In this example, assume that when the clinician increased the ECAP threshold to be above 100 microvolts, patient 12 began to experience discomfort. In this case, the clinician may identify the ECAP threshold as 100 microvolts for the 60 microsecond pulse width of the stimulation.

The clinician may then set the pulse width at 2000 microsecond, and may increase the ECAP threshold starting from 50 microvolts. As the clinician is increasing the ECAP threshold, processing circuit 210 may adjust the amplitude of the stimulation so that the ECAP that is generated is approximately equal to the ECAP threshold. In this example, assume that when the clinician went above 80 microvolts for the ECAP threshold, patient 12 began to experience discomfort. In this case, the clinician may identify the ECAP threshold as 80 microvolts for 2000 microseconds pulse width.

During normal operation, once the ECAP thresholds 220 have been stored, processing circuit 210 may select the appropriate ECAP threshold from ECAP thresholds 220. As an example, prior to adjustment of stimulation, processing circuit 210 may determine the value to which the first therapy parameter will be adjusted (e.g., the second level if the first therapy parameter is to be adjusted from the first level to the second level). Processing circuit 210 may then evaluate ECAP thresholds 220 to identify the ECAP threshold associated with the second level, and set the ECAP threshold to the identified ECAP threshold. Processing circuit 210 may then adjust the second therapy parameter from the third level to the fourth level so that delivery of the therapy with the first therapy parameter at the second level and the second therapy parameter at the fourth level results in ECAP that is approximately equal to the ECAP threshold.

In the above example, the ECAP threshold was set based on the second level. However, the techniques are not so limited. In some examples, processing circuit 210 may determine a rate at which to adjust the first therapy parameter from the first level to the second level. Processing circuit 210 may then evaluate ECAP thresholds 220 to identify the ECAP threshold that is associated with determined rate. Processing circuit 210 may then adjust the second therapy parameter from the third level to the fourth level so that delivery of the therapy with the first therapy parameter at the second level and the second therapy parameter at the fourth level results in ECAP that is approximately equal to the ECAP threshold.

Also, in some examples, rather than or in addition to evaluating ECAP thresholds 220 to set the ECAP threshold, processing circuit 210 may utilize additional techniques to set the ECAP threshold. As one example, processing circuit 210 may periodically change the ECAP threshold plus or minus 10%, which will cause a change in the therapy that is delivered because processing circuit 210 will adjust the second therapy parameter to ensure that the generated ECAP is approximately equal to the ECAP threshold. This would be another way in which accommodation may be avoided. There are other ways in which to set the ECAP threshold and the techniques are not limited to the above examples.

In some examples, processing circuit 210 may continuously adjust the second therapy parameter during the adjustment of the first therapy parameter. As processing circuit 210 is adjusting the first therapy parameter, processing circuit 210 may cause stimulation circuit 202 to deliver therapy. For instance, processing circuit 210 may adjust the first therapy parameter from a first level to a second level over a certain time period and at a certain step size. In this example, after adjusting the first therapy parameter by the step size, processing circuit 210 may adjust the second therapy parameter so that the generated ECAP is approximately equal to the ECAP threshold. For instance, processing circuit 210 may determine the ECAP level after the delivery of a pulse for comparison with the ECAP threshold. Processing circuit 210 may repeat these operations after every step size adjustment.

Rather than continuous adjustment of the second therapy parameter in a series of increments (e.g., fixed or variable increments), in some examples, processing circuit 210 may discretely adjust the second therapy parameter. For example, processing circuit 210 may first completely adjust the first therapy parameter from the first level to the second level. Once the first therapy parameter is at the second level, processing circuit 210 may adjust the second therapy parameter from the third level to the fourth level (e.g., based on ECAP generated after delivery of a pulse).

This disclosure contemplates both continuous (e.g., adjustment is slowly ramped up or down) and discrete adjustment (adjustment is ramped by discrete levels), as alternatives, as well as any intermediate adjustment. For instance, processing circuit 210 may adjust the first therapy parameter from the first level to the second level. Responsive to the adjustment of the first therapy parameter, processing circuit 210 may compare a level of the ECAP generated from therapy delivery, and adjust the second therapy parameter from a third level to a fourth level based on the comparison. Such disclosure, unless specifically stated otherwise, encompasses the example where processing circuit 210 continuously compares the level of the ECAP generated from therapy delivery to the ECAP threshold during adjustment of the first therapy parameter, and continuously adjusts the second therapy parameter in a series of increments during the adjustment of the first therapy parameter. Such disclosure also encompasses the example where processing circuit 210 first adjusts the first therapy parameter from the first level to the second level, and then adjusts the second therapy parameter from the third level to the fourth level.

Figure 4:
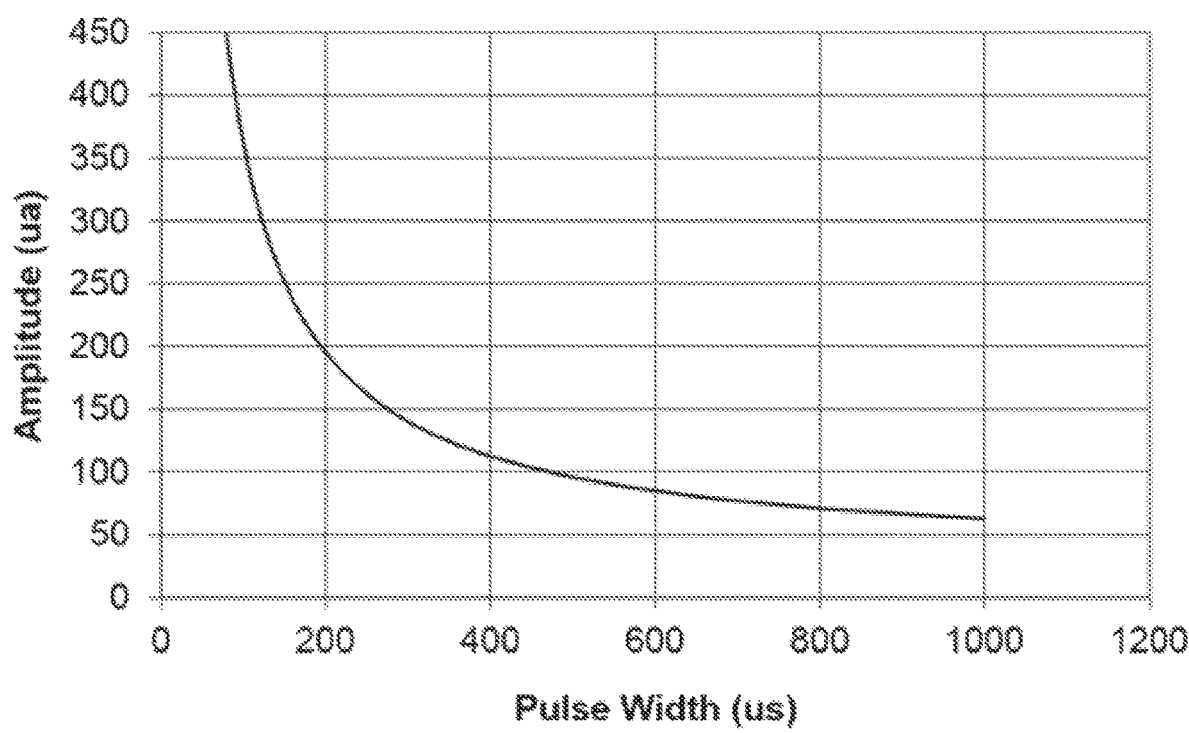
FIG. 4 is a graph illustrating strength duration curve for threshold stimulation.

FIGS. 3A-3C are timing diagrams illustrating an example operation for therapy adjustment according to the techniques of this disclosure. FIG. 4 is a graph illustrating strength duration curve for threshold stimulation. FIGS. 3A-3C and FIG. 4 are described together.

Assume that the pulse width (e.g., first therapy parameter) is at W1, and the amplitude (e.g., second therapy parameter) is at A1. Assume that IMD 102 has been delivering therapy with pulse width at W1 and amplitude at A1 for a certain amount of time. To avoid or reduce the likelihood of accommodation, processing circuit 210 may adjust the pulse width from W1 at time T1 to W2 at time T2, as illustrated in FIG. 3A.

In response to processing circuit 210 adjusting the pulse width, processing circuit 210 compares the ECAP that is generated in response to therapy delivery to an ECAP threshold, as illustrated in FIG. 3B. Based on the comparison, processing circuit 210 adjusts the amplitude from A1 to A2, as illustrated in FIG. 3C.

There may be various ways with which processing circuit 210 may determine the amplitude A2. For example, FIG. 4 illustrates an example curve that shows amplitude in microamps of stimulation current for different pulse widths that provide approximately the same ability to create an action potential. In other words, the illustrated curve illustrates combinations of current levels and pulse widths that evoke the same action potential.

For instance, at 200 microsecond pulse width and amplitude of 200 microamps, the ability to create an action potential on a neuron is same as a 450 microsecond pulse width and amplitude of 100 microamps. Since only about 5% of the energy gets to the spinal cord, a program parameter to achieve 100 microamps at the spinal cord needs to have therapy parameter of approximately 2 milliamps.

Accordingly, in one example, processing circuit 210 may adjust the pulse width from W1 at time T1 to W2 at time T2, as illustrated in FIG. 3A. Then, processing circuit 210 may determine the amplitude A2 based on the strength duration curve illustrated in FIG. 4 based on the pulse width W2. For instance, assume that processing circuit 210 adjusted the pulse width from 200 microseconds to 450 microseconds. In this example, processing circuit 210 may select the amplitude to be 2 milliamps so that 100 microamps is delivered to the spinal cord.

The values of the curve illustrated in FIG. 4 may be stored as a lookup table in memory 211, and processing circuit 210 may select values for the pulse width and amplitude based on the values stored in the lookup table. Processing circuit 210 may use interpolation (such as linear interpolation as one example) to determine intermediate values not stored in the lookup table. As another example, memory 211 may store an equation for generating the curve illustrated in FIG. 4, and processing circuit 210 may determine the values of the curve based on the equation. There may be other ways in which processing circuit 210 may determine the values of the curve illustrated in FIG. 4, and the example techniques are not limited to the illustrated examples.

However, as processing circuit 210 increases pulse width, as illustrated in FIG. 3A, the generated level of the ECAP may become greater than the ECAP threshold, as illustrated in FIG. 3B. In response, processing circuit 210 may decrease the amplitude of the stimulation, as illustrated in FIG. 3C. It may be possible that processing circuit 210 reduces the amplitude so much that even though the pulse width is getting larger, the generated level of the ECAP is less than the ECAP threshold. In response, processing circuit 210 may begin to increase the amplitude until the level of the ECAP become greater than the ECAP threshold.

In this way, as illustrated in FIG. 3C, the amplitude may oscillate a little bit but with a downward trajectory indicating the reduction in the amplitude from A1 to A2. At time T2, the pulse width is at W2, and the amplitude is at A2, and the level of the ECAP is approximately equal to the ECAP threshold. Accordingly, the example techniques provide for therapy adjustment to avoid or reduce accommodation. As illustrated in FIGS. 3B and 3C, in some examples, processing circuit 210 may control the therapy adjustment such that the generated ECAP does not deviate too much from the ECAP threshold meaning that patient 12 may not experience discomfort, allowing for such adjustments to occur at home rather than via a clinic visit, and occur more periodically. Although FIGS. 3A-3C illustrate adjustment of pulse width, and then adjustment of amplitude based on comparison to ECAP threshold, in some examples, processing circuit 210 may adjust amplitude, and then adjust pulse width based on comparison to ECAP threshold (e.g., based on the curve illustrated in FIG. 4).

Figure 5:
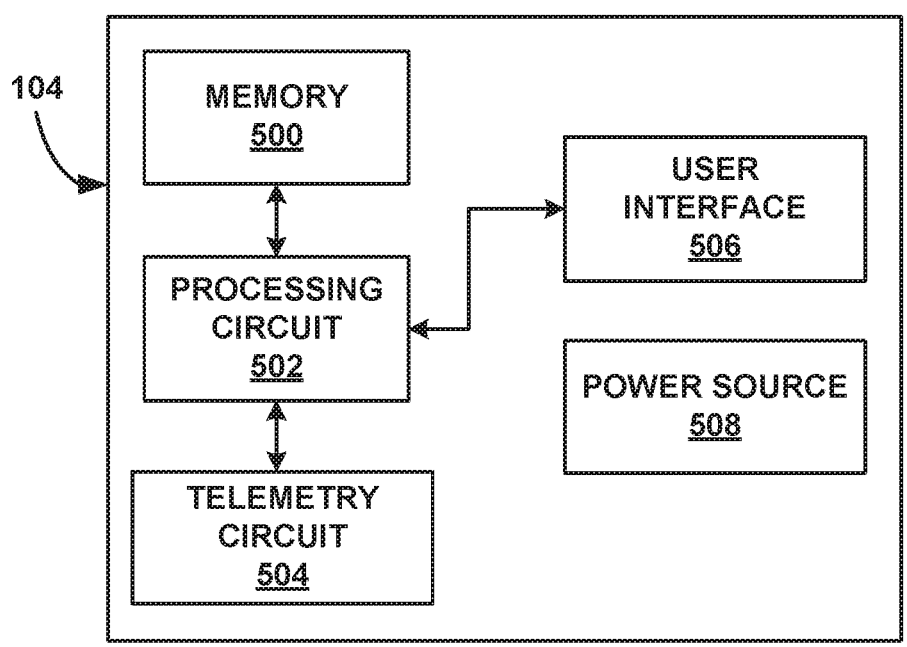
FIG. 5 is a functional block diagram illustrating components of an example external programmer that may communicate with the medical device of FIG. 2.

FIG. 5 is a functional block diagram illustrating components of an example external programmer 104. External programmer 104 may operate as a patient programmer or clinician programmer configured to permit a user to program and/or control therapy parameter values of IMD 102. External programmer 104 includes memory 500, processing circuit 502, telemetry circuit 504, user interface 506, and power source 508.

Processing circuit 502 controls user interface 506 and telemetry circuit 504, and stores and retrieves information and instructions to and from memory 500. Programmer 104 may be configured for use as a clinician programmer or a patient programmer. Processing circuit 502 may comprise any combination of one or more processors including one or more microprocessors, DSPs, ASICs, FPGAs, or other equivalent integrated or discrete logic circuitry. Accordingly, processing circuit 502 may include any suitable structure, whether in hardware, software, firmware, or any combination thereof, to perform the functions ascribed herein to processing circuit 502.

In some examples, processing circuit 502 may be configured to perform the example operations described above with respect to processing circuit 210. For example, processing circuit 502 may output information to processing circuit 210 defining a first level for the first therapy parameter, and output information defining a third level for the second therapy parameter. Processing circuit 502 may receive information indicating the level of a sensed ECAP generated in response to therapy delivered with the adjusted first therapy parameter, and may compare the level of the ECAP to the ECAP threshold. Processing circuit 502 may then output information to processing circuit 210 defining the second level for the first therapy parameter and the fourth level for the second therapy parameter. Processing circuit 210 may then adjust the second therapy parameter from the third level to the fourth level.

In some examples, one or more of the operations performed by processing circuit 210, as described above with respect to FIGS. 2, 3A-3C, and 4, may be performed by processing circuit 502. In some examples, processing circuit 210 and processing circuit 502 may split operations (e.g., processing circuit 210 performs the adjustment to therapy parameters, and processing circuit 502 performs the comparison of the level of ECAP to the ECAP threshold). Processing circuit 502 may also define the therapy parameters and the levels to which the therapy parameters are to be adjusted by processing circuit 210. In some cases, processing circuit 502 may define the therapy parameters, and processing circuit 210 may determine the level to which the therapy parameters are to be adjusted. Accordingly, description in this disclosure of a processing circuit performing operations means processing circuit 210 performing the operations, processing circuit 502 performing the operations, or a combination of processing circuit 210 and processing circuit 502 performing the operations.

A user, such as a clinician or patient 12, may interact with programmer 104 through user interface 506. User interface 506 includes a display (not shown), such as a LCD or LED display or other type of screen, with which processing circuit 502 may present information related to the therapy. In addition, user interface 506 may include an input mechanism to receive input from the user. The input mechanisms may include, for example, buttons, a keypad (e.g., an alphanumeric keypad), a peripheral pointing device or another input mechanism that allows the user to navigate through user interfaces presented by processing circuit 502 of programmer 104 and provide input.

If programmer 104 includes buttons and a keypad, the buttons may be dedicated to performing a certain function (i.e., a power button), or the buttons and the keypad may be soft keys that change function depending upon the section of the user interface currently viewed by the user. In addition, or instead, the screen (not shown) of programmer 104 may be a touch screen that allows the user to provide input directly to the user interface shown on the display. The user may use a stylus or their finger to provide input to the display. In other examples, user interface 506 also includes audio circuitry for providing audible notifications, instructions or other sounds to patient 12, receiving voice commands from patient 12, which may be useful if patient 12 has limited motor functions, or both. Patient 12, a clinician or another user may also interact with programmer 104 to manually select therapy programs, generate new therapy programs, modify therapy programs through individual or global adjustments, and transmit the new programs to IMD 102.

Memory 500 may include instructions for operating processing circuit 502, user interface 506, and telemetry circuit 504, and for managing power source 508. In some examples, memory 500 may also store any therapy data retrieved from IMD 102 during the course of therapy, such as biomarker information, sensed bioelectrical brain signals, and the like. In some instances, the clinician may use this therapy data to determine the progression of the patient condition in order to plan future treatment for the movement disorder (or other patient condition) of patient 12. Memory 500 may include any volatile or nonvolatile memory, such as RAM, ROM, EEPROM or flash memory. Memory 500 may also include a removable memory portion that may be used to provide memory updates or increases in memory capacities. A removable memory may also allow sensitive patient data to be removed before programmer 104 is used by a different patient.

Wireless telemetry in programmer 104 may be accomplished by RF communication or proximal inductive interaction of external programmer 104 with IMD 102. This wireless communication is possible through the use of telemetry circuit 504. Accordingly, telemetry circuit 504 may be similar to the telemetry circuit contained within IMD 102. In other examples, programmer 104 may be capable of infrared communication or direct communication through a wired connection. In this manner, other external devices may be capable of communicating with programmer 104 without needing to establish a secure wireless connection.

Power source 508 is configured to deliver operating power to the components of programmer 104. Power source 508 may include a battery and a power generation circuit to produce the operating power. In some examples, the battery may be rechargeable to allow extended operation. Recharging may be accomplished by electrically coupling power source 508 to a cradle or plug that is connected to an alternating current (AC) outlet. In addition, recharging may be accomplished through proximal inductive interaction between an external charger and an inductive charging coil within programmer 104. In other examples, traditional batteries (e.g., nickel cadmium or lithium ion batteries) may be used. In addition, programmer 104 may be directly coupled to an alternating current outlet to operate.

Figure 6:
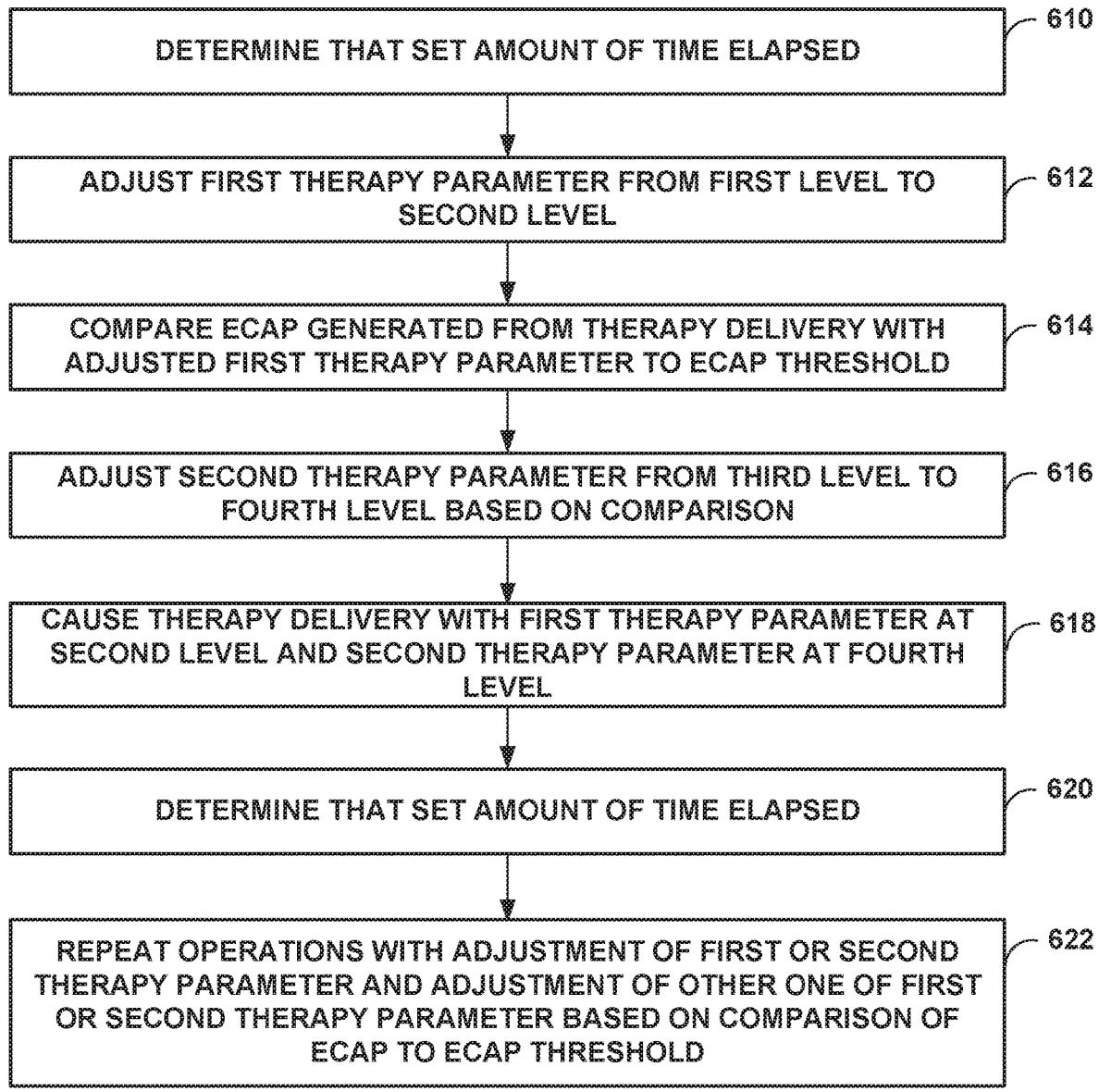
FIG. 6 is a flowchart illustrating an example operation for therapy delivery according to the techniques of this disclosure.

FIG. 6 is a flowchart illustrating an example operation for therapy delivery according to the techniques of this disclosure. The example techniques of FIG. 6 are described with respect to a processing circuit. Examples of the processing circuit include processing circuit 210, processing circuit 502, or a combination of processing circuit 210 and processing circuit 502. Accordingly, where operations can be performed by a combination of processing circuit 210 and processing circuit 502, the term processing circuit means processing circuit 210, processing circuit 502, or a combination. Where operations can be performed only by one of processing circuit 210 or processing circuit 502, the term processing circuit means processing circuit 210 or processing circuit 502.

As illustrated, a processing circuit may determine that a set amount of time elapsed (610). This set amount of time may be based on a set period or a randomly generated number, and in general less than the time needed for patient 12 to become accommodated to the therapy.

The processing circuit may adjust the first therapy parameter from a first level to a second level after the determined amount of time elapsed (612). As one example, processing circuit 210 may adjust the amplitude of the therapy (e.g., amplitude is the first therapy parameter). As another example, processing circuit 210 may adjust the pulse width of the therapy (e.g., pulse width is the first therapy parameter). Processing circuit 210 may also determine the rate at which to adjust the first therapy parameter, and generally the manner in which to adjust the first therapy parameter (e.g., step size of the adjustment). Processing circuit 210 may receive information indicating the first level of the first therapy parameter from processing circuit 502, and may determine the second level for the first therapy parameter. In some examples, processing circuit 210 may receive information indicating the first level of the first therapy parameter from processing circuit 502, and may also receive information indicating the second level for the first therapy parameter.

Responsive to the adjustment of the first therapy parameter, processing circuit 210 may compare a level of an ECAP, sensed via at least one of the one or more leads 16, generated from therapy delivery based on the adjusted first therapy parameter to an ECAP threshold (614). In some examples, processing circuit 210 may continuously compare the level of the ECAP generated from therapy delivery to the ECAP threshold during the adjustment of the first therapy parameter.

For example, processing circuit 210 may select the second level to which the first therapy parameter is to be adjusted prior to adjusting the first therapy parameter from the first level to the second level, and processing circuit 210 may set the ECAP threshold based on the selected second level. In this example, processing circuit 210 may compare the level of the ECAP to the ECAP threshold that is set based on the selected second level. As another example, processing circuit 210 may determine a rate at which to adjust the first therapy parameter from the first level to the second level, and processing circuit 210 may set the ECAP threshold based on the determined rate. In this example, processing circuit 210 may compare the level of the ECAP to the ECAP threshold that is set based on the determined rate. In some examples, processing circuit 210 may select the second level based on information transmitted by processing circuit 502, but processing circuit 210 may select the second level without needing information from processing circuit 502 of the second level in some examples.

In some examples, processing circuit 210 may compare the level of the ECAP to the ECAP threshold after delivery of each pulse of the therapy. Also, the ECAP threshold may be a non-zero numerical value.

The processing circuit may adjust a second therapy parameter from a third level to a fourth level based on the comparison (616). Processing circuit 210 may continuously adjust the second therapy parameter during the adjustment of the first therapy parameter in some but not necessarily all examples. In some examples, responsive to adjusting the first therapy parameter and prior to adjusting the second therapy parameter from the third level to the fourth level, processing circuit 210 may have adjusted the second therapy parameter from a fifth level to the third level based on a therapy table. In such examples, the second therapy parameter is adjusted from the third level to the fourth level after being adjusted from the fifth level to the third level. It should be understood that first, second, third, fourth, etc. as used to describe one or more examples in this disclosure are merely enumerative, and do not imply relative values (e.g., higher to lower in level).

As one example, processing circuit 210 may determine that the level of the ECAP is greater than the ECAP threshold based on the comparison. In this example, processing circuit 210 may, responsive to determining that the level of the ECAP is greater than the ECAP threshold, adjust the second therapy parameter from the third level to the fourth level. In this example, the level of the ECAP is less than or equal to the ECAP threshold when the therapy is delivered with the second therapy parameter at the fourth level.

As another example, processing circuit 210 may determine that the level of the ECAP is less than the ECAP threshold based on the comparison. In this example, processing circuit 210 may, responsive to determining that the level of the ECAP is less than the ECAP threshold, adjust the second therapy parameter from the third level to the fourth level. In this example, the level of the ECAP is approximately equal (e.g., within 10%) to the ECAP threshold when the therapy is delivered with the second therapy parameter at the fourth level.

As described above, in some examples, processing circuit 502 may perform the comparisons based on information of the level of ECAP received from IMD 102. Also, in some examples, processing circuit 502 may output information indicating the third level for the second therapy parameter, and processing circuit 210 may determine the fourth level for the second therapy parameter. In some examples, processing circuit 502 may output information indicating the third level for the second therapy parameter, and output information indicating the fourth level for the second therapy parameter.

The processing circuit may cause stimulation circuit 204 to deliver therapy with the first therapy parameter at the second level and the second therapy parameter at the fourth level (618). In this way, there is adjustment to the therapy to avoid accommodation but with less likelihood of discomfort to the patient.

The processing circuit may determine that another set amount of time has elapsed (620). In response, the processing circuit may repeat the operations with adjustment of first or second therapy parameter and adjustment of other one of first and second therapy parameter based on comparison of level of the ECAP to ECAP threshold (622). In this way, the processing circuit may keep adjusting the therapy parameters to avoid accommodation.

For instance, assume that the ECAP threshold was a first ECAP threshold. Subsequent to causing therapy delivery with the first therapy parameter at the second level and the second therapy parameter at the fourth level, the processing circuit may determine that an additional amount of time elapsed. The processing circuit may adjust the first therapy parameter from the second level to a fifth level, and in response to adjusting the first therapy parameter, compare a level of a second ECAP generated from therapy delivery to a second ECAP threshold. The processing circuit may adjust the second therapy parameter from the fourth level to a sixth level based on the comparison of the level of the second ECAP to the second ECAP threshold, and cause therapy delivery with the first therapy parameter at the fifth level and the second therapy parameter at the sixth level.

In the above example, the first therapy parameter was adjusted, and the second therapy parameter was adjusted in response to adjustment of the first therapy parameter. Then, after additional time elapsed, the first therapy parameter was again adjusted, and the second therapy parameter was adjusted in response to the adjustment of the first therapy parameter. However, the example techniques are not so limited. For instance, the first therapy parameter may be adjusted, and the second therapy parameter may be adjusted in response. Then, rather than adjusting the first parameter again, the second therapy parameter may be adjusted, and the first therapy parameter is adjusted in response.

For example, subsequent to causing therapy delivery with the first therapy parameter at the second level and the second therapy parameter at the fourth level, the processing circuit may determine that an additional amount of time elapsed. The processing circuit may adjust the second therapy parameter from the third level to a fifth level, and in response to adjusting the second therapy parameter, compare a level of a second ECAP generated from therapy delivery to a second ECAP threshold. The processing circuit may adjust the first therapy parameter from the second level to a sixth level based on the comparison of the level of the second ECAP to the second ECAP threshold, and cause therapy delivery with the first therapy parameter at the sixth level and the second therapy parameter at the fifth level.

The example techniques are described with respect to comparing the level of ECAP to an ECAP threshold to determine adjustment in therapy parameters. However, the example techniques are not so limited, and measuring of ECAPs may not be necessary in all examples.

As one example, processing circuit 210 or processing circuit 502 may use the values from the strength duration curve illustrated in FIG. 4 to set the therapy parameters regardless of whether action potentials are evoked. For instance, referring back to FIG. 3A, the processing circuit may adjust the pulse width from W1 at time T1 to W2 at time T2. However, during the adjustment of the pulse width, the processing circuit may not compare the level of ECAP to an ECAP threshold. Rather, based on the strength duration curve, the processing circuit may select the amplitude A2, as illustrated in FIG. 3C, and may ramp down (or up if needed) the stimulation amplitude until the stimulation amplitude is at A2. It should be understood that rather than ramping, the processing circuit may increase or decrease the pulse width and amplitude using discrete levels or directly set the pulse width to W2 and amplitude to A2 without passing through any intermediate levels.

In this manner, the processing circuit may address accommodation without the need for sensing ECAPs. For instance, because the amplitude/pulse width combinations of the curve in FIG. 4 generate the same level of ECAP, but setting therapy based on the curve, processing circuit 210 may keep the level of ECAP the same, but change therapy so that patient 12 does not become accommodated with the therapy.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, circuits or components may be implemented together or separately as discrete but interoperable logic devices. Depiction of different features as circuits or units is intended to highlight different functional aspects and does not necessarily imply that such circuits or units must be realized by separate hardware or software components. Rather, functionality associated with one or more circuits or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

What is claimed is:

1. A method of therapy delivery, the method comprising:
determining that a set amount of time has elapsed;
adjusting a first therapy parameter from a first level to a second level different than the first level after the set amount of time has elapsed;
responsive to the adjustment of the first therapy parameter, comparing a level of an evoked compound action potential (ECAP) generated in response to therapy delivered with the adjusted first therapy parameter to an ECAP threshold;
adjusting a second therapy parameter from a third level to a fourth level different than the third level based on the comparison, wherein the second therapy parameter is different than the first therapy parameter; and
causing delivery of the therapy with the first therapy parameter at the second level and the second therapy parameter at the fourth level.

2. The method of claim 1, further comprising:
determining that the level of the ECAP is greater than the ECAP threshold based on the comparison,
wherein adjusting the second therapy parameter comprises, responsive to determining that the level of the ECAP is greater than the ECAP threshold, adjusting the second therapy parameter from the third level to the fourth level, wherein the level of the ECAP is less than or equal to the ECAP threshold when the therapy is delivered with the second therapy parameter at the fourth level.

3. The method of claim 1, further comprising:
determining that the level of the ECAP is less than the ECAP threshold based on the comparison,
wherein adjusting the second therapy parameter comprises, responsive to determining that the level of the ECAP is less than the ECAP threshold, adjusting the second therapy parameter from the third level to the fourth level, wherein the level of the ECAP is approximately equal to the ECAP threshold when the therapy is delivered with the second therapy parameter at the fourth level.

4. The method of claim 1, further comprising:
responsive to adjusting the first therapy parameter and prior to adjusting the second therapy parameter from the third level to the fourth level, adjusting the second therapy parameter from a fifth level to the third level based on a therapy table, wherein the second therapy parameter is adjusted from the third level to the fourth level after being adjusted from the fifth level to the third level.

5. The method of claim 1, wherein the therapy is electrical stimulation, the first therapy parameter comprises pulse width of the electrical stimulation, and wherein the second therapy parameter comprises voltage amplitude or current amplitude of the electrical stimulation.

6. The method of claim 1, wherein the therapy is electrical stimulation, the first therapy parameter comprises voltage amplitude or current amplitude of the electrical stimulation, and wherein the second therapy parameter comprises pulse width of the electrical stimulation.

7. The method of claim 1, further comprising:
selecting the second level prior to adjusting the first therapy parameter from the first level to the second level; and
setting the ECAP threshold based on the selected second level,
wherein comparing the level of the ECAP to the ECAP threshold comprises comparing the level of the ECAP to the ECAP threshold that is set based on the selected second level.

8. The method of claim 1, further comprising:
determining a rate at which to adjust the first therapy parameter from the first level to the second level; and
setting the ECAP threshold based on the determined rate,
wherein comparing the level of the ECAP to the ECAP threshold comprises comparing the level of the ECAP to the ECAP threshold that is set based on the determined rate.

9. The method of claim 1, wherein the ECAP comprises a first ECAP, and wherein the ECAP threshold comprises a first ECAP threshold, the method further comprising:
subsequent to causing delivery of the therapy with the first therapy parameter at the second level and the second therapy parameter at the fourth level, determining that an additional amount of time elapsed; and
in response to determining that the additional amount of time elapsed:
adjusting the first therapy parameter from the second level to a fifth level different than the second level;
in response to adjusting the first therapy parameter, comparing a level of a second ECAP generated from delivery of the therapy with the first therapy parameter at the fifth level to a second ECAP threshold;
adjusting the second therapy parameter from the fourth level to a sixth level different than the fourth level based on the comparison of the level of the second ECAP to the second ECAP threshold; and
causing delivery of the therapy with the first therapy parameter at the fifth level and the second therapy parameter at the sixth level.

10. The method of claim 1, wherein the ECAP comprises a first ECAP, and wherein the ECAP threshold comprises a first ECAP threshold, the method further comprising:
subsequent to causing delivery of the therapy with the first therapy parameter at the second level and the second therapy parameter at the fourth level, determining that an additional amount of time elapsed;
in response to determining that the additional amount of time elapsed:
adjusting the second therapy parameter from the third level to a fifth level different than the third level;
in response to adjusting the second therapy parameter, comparing a level of a second ECAP generated from delivery of the therapy with the first therapy parameter at the fifth level to a second ECAP threshold;
adjusting the first therapy parameter from the second level to a sixth level different than the sixth level based on the comparison of the level of the second ECAP to the second ECAP threshold; and
causing delivery of the therapy with the first therapy parameter at the sixth level and the second therapy parameter at the fifth level.

11. The method of claim 1, wherein the therapy comprises stimulation pulses, and comparing the level of the ECAP to the ECAP threshold comprises comparing the level of the ECAP to the ECAP threshold after delivery of each stimulation pulse of the therapy.

12. The method of claim 1, wherein comparing comprises continuously comparing the level of the ECAP generated in response to the delivery of the therapy to the ECAP threshold during the adjustment of the first therapy parameter, and wherein adjusting the second therapy parameter comprises continuously adjusting the second therapy parameter during the adjustment of the first therapy parameter.

13. The method of claim 1, wherein the ECAP threshold is a non-zero numerical value.

14. A device for therapy delivery, the device comprising:
a stimulation circuit; and
a processing circuit configured to:
  determine that a set amount of time has elapsed;
  adjust a first therapy parameter from a first level to a second level different than the first level after the set amount of time has elapsed;
  responsive to the adjustment of the first therapy parameter, compare a level of an evoked compound action potential (ECAP) generated in response to therapy delivered with the adjusted first therapy parameter to an ECAP threshold;
  adjust a second therapy parameter from a third level to a fourth level different than the third level based on the comparison, wherein the second therapy parameter is different than the first therapy parameter; and
  cause the stimulation circuit to deliver therapy with the first therapy parameter at the second level and the second therapy parameter at the fourth level.

15. The device of claim 14, wherein the processing circuit is configured to:
  determine that the level of the ECAP is greater than the ECAP threshold based on the comparison,
  wherein to adjust the second therapy parameter, the processing circuit is configured to, responsive to determining that the level of the ECAP is greater than the ECAP threshold, adjust the second therapy parameter from the third level to the fourth level, wherein the level of the ECAP is less than or equal to the ECAP threshold when the therapy is delivered with the second therapy parameter at the fourth level.

16. The device of claim 14, wherein the processing circuit is configured to:
  determine that the level of the ECAP is less than the ECAP threshold based on the comparison,
  wherein to adjust the second therapy parameter, the processing circuit is configured to, responsive to determining that the level of the ECAP is less than the ECAP threshold, adjust the second therapy parameter from the third level to the fourth level, wherein the level of the ECAP is approximately equal to the ECAP threshold when the therapy is delivered with the second therapy parameter at the fourth level.

17. The device of claim 14, wherein the processing circuit is configured to:
  responsive to adjusting the first therapy parameter and prior to adjusting the second therapy parameter from the third level to the fourth level, adjust the second therapy parameter from a fifth level to the third level based on a therapy table, wherein the second therapy parameter is adjusted from the third level to the fourth level after being adjusted from the fifth level to the third level.

18. The device of claim 14, wherein the therapy is electrical stimulation, the first therapy parameter comprises pulse width of the electrical stimulation, and wherein the second therapy parameter comprises voltage amplitude or current amplitude of the electrical stimulation.

19. The device of claim 14, wherein the therapy is electrical stimulation, the first therapy parameter comprises voltage amplitude or current amplitude of the electrical stimulation, and wherein the second therapy parameter comprises pulse width of the electrical stimulation.

20. The device of claim 14, wherein the processing circuit is configured to:
  select the second level prior to adjusting the first therapy parameter from the first level to the second level; and
  set the ECAP threshold based on the selected second level,
  wherein to compare the level of the ECAP to the ECAP threshold, the processing circuit is configured to compare the level of the ECAP to the ECAP threshold that is set based on the selected second level.

21. The device of claim 14, wherein the processing circuit is configured to:
  determine a rate at which to adjust the first therapy parameter from the first level to the second level; and
  set the ECAP threshold based on the determined rate,
  wherein to compare the level of the ECAP to the ECAP threshold, the processing circuit is configured to compare the level of the ECAP to the ECAP threshold that is set based on the determined rate.

22. The device of claim 14, wherein the ECAP comprises a first ECAP, wherein the ECAP threshold comprises a first ECAP threshold, and wherein the processing circuit is configured to:
  subsequent to causing delivery of the therapy with the first therapy parameter at the second level and the second therapy parameter at the fourth level, determine that an additional amount of time elapsed; and
  in response to determining that the additional amount of time elapsed:
    adjust the first therapy parameter from the second level to a fifth level different than the second level;
    in response to adjusting the first therapy parameter, compare a level of a second ECAP generated from delivery of the therapy with the first therapy parameter at the fifth level to a second ECAP threshold;
    adjust the second therapy parameter from the fourth level to a sixth level different than the fourth level based on the comparison of the level of the second ECAP to the second ECAP threshold; and
    cause the stimulation circuit to deliver the therapy with the first therapy parameter at the fifth level and the second therapy parameter at the sixth level.

23. The device of claim 14, wherein the ECAP comprises a first ECAP, wherein the ECAP threshold comprises a first ECAP threshold, and wherein the processing circuit is configured to:
  subsequent to causing delivery of the therapy with the first therapy parameter at the second level and the second therapy parameter at the fourth level, determine that an additional amount of time elapsed;
  in response to determining that the additional amount of time elapsed:
    adjust the second therapy parameter from the third level to a fifth level different than the third level;
    in response to adjusting the second therapy parameter, compare a level of a second ECAP generated from delivery of the therapy with the first therapy parameter at the fifth level to a second ECAP threshold;

adjust the first therapy parameter from the second level to a sixth level different than the sixth level based on the comparison of the level of the second ECAP to the second ECAP threshold; and
cause the stimulation circuit to deliver the therapy with the first therapy parameter at the sixth level and the second therapy parameter at the fifth level.

24. The device of claim 14, wherein the therapy comprises stimulation pulses, and wherein to compare the level of the ECAP to the ECAP threshold, the processing circuit is configured to compare the level of the ECAP to the ECAP threshold after delivery of each stimulation pulse of the therapy.

25. The device of claim 14, wherein to compare, the processing circuit is configured to continuously compare the level of the ECAP generated in response to the delivery of the therapy to the ECAP threshold during the adjustment of the first therapy parameter, and wherein to adjust the second therapy parameter, the processing circuit is configured to continuously adjust the second therapy parameter during the adjustment of the first therapy parameter.

26. The device of claim 14, wherein the ECAP threshold is a non-zero numerical value.

27. A computer-readable storage medium storing instructions thereon that when executed cause one or more processors of a device for therapy delivery to:
determine that a set amount of time has elapsed;
adjust a first therapy parameter from a first level to a second level different than the first level after the set amount of time has elapsed;
responsive to the adjustment of the first therapy parameter, compare a level of an evoked compound action potential (ECAP) generated in response to therapy delivered with the adjusted first therapy parameter to an ECAP threshold;
adjust a second therapy parameter from a third level to a fourth level different than the third level based on the comparison, wherein the second therapy parameter is different than the first therapy parameter; and
cause delivery of the therapy with the first therapy parameter at the second level and the second therapy parameter at the fourth level.

28. The computer-readable storage medium of claim 27, further comprising instructions that cause the one or more processors to:
select the second level prior to adjusting the first therapy parameter from the first level to the second level; and
set the ECAP threshold based on the selected second level,
wherein the instructions that cause the one or more processors to compare the level of the ECAP to the ECAP threshold comprise instructions that cause the one or more processors to compare the level of the ECAP to the ECAP threshold that is set based on the selected second level.

29. The computer-readable storage medium of claim 27, further comprising instructions that cause the one or more processors to:
determine a rate at which to adjust the first therapy parameter from the first level to the second level; and
set the ECAP threshold based on the determined rate,
wherein the instructions that cause the one or more processors to compare the level of the ECAP to the ECAP threshold comprise instructions that cause the one or more processors to compare the level of the ECAP to the ECAP threshold that is set based on the determined rate.

30. A device for therapy delivery, the device comprising:
means for determining that a set amount of time has elapsed;
means for adjusting a first therapy parameter from a first level to a second level different than the first level after the set amount of time has elapsed;
responsive to the adjustment of the first therapy parameter, means for comparing a level of an evoked compound action potential (ECAP) generated in response to therapy delivered with the adjusted first therapy parameter to an ECAP threshold;
means for adjusting a second therapy parameter from a third level to a fourth level different than the third level based on the comparison, wherein the second therapy parameter is different than the first therapy parameter; and
means for causing delivery of the therapy with the first therapy parameter at the second level and the second therapy parameter at the fourth level.

31. The device of claim 30, further comprising:
means for determining that the level of the ECAP is greater than the ECAP threshold based on the comparison,
wherein the means for adjusting the second therapy parameter comprises means for adjusting the second therapy parameter from the third level to the fourth level responsive to determining that the level of the ECAP is greater than the ECAP threshold, wherein the level of the ECAP is less than or equal to the ECAP threshold when the therapy is delivered with the second therapy parameter at the fourth level.

32. The device of claim 30, further comprising:
means for determining that the level of the ECAP is less than the ECAP threshold based on the comparison,
wherein the means for adjusting the second therapy parameter comprises means for adjusting the second therapy parameter from the third level to the fourth level responsive to determining that the level of the ECAP is less than the ECAP threshold, wherein the level of the ECAP is approximately equal to the ECAP threshold when the therapy is delivered with the second therapy parameter at the fourth level.

33. A system for therapy delivery, the system comprising:
an implantable medical device (IMD) comprising a stimulation circuit;
one or more leads coupled to the IMD; and
a processing circuit configured to:
determine that a set amount of time has elapsed;
adjust a first therapy parameter from a first level to a second level different than the first level after the set amount of time has elapsed;
responsive to the adjustment of the first therapy parameter, compare a level of an evoked compound action potential (ECAP), sensed via at least one of the one or more leads, generated in response to therapy delivered with the adjusted first therapy parameter to an ECAP threshold;
adjust a second therapy parameter from a third level to a fourth level different than the third level based on the comparison, wherein the second therapy parameter is different than the first therapy parameter; and
cause the stimulation circuit to deliver therapy with the first therapy parameter at the second level and the second therapy parameter at the fourth level via at least one of the one or more leads.

34. The system of claim 33, wherein the IMD comprises the processing circuit.

35. The system of claim 33, further comprising an external programmer configured to program the IMD, wherein the external programmer is configured to transmit information indicating the first level of the first therapy parameter and the third level for the second therapy parameter, and wherein the processing circuit is configured to determine the second level for the first therapy parameter and the fourth level for the second therapy parameter.

36. The system of claim 33, further comprising an external programmer configured to program the IMD, wherein the external programmer is configured to transmit information indicating one or more of the first level of the first therapy parameter, the third level for the second therapy parameter, the second level for the first therapy parameter, and the fourth level for the second therapy parameter.

37. The system of claim 33, wherein the processing circuit is configured to:
select the second level prior to adjusting the first therapy parameter from the first level to the second level; and
set the ECAP threshold based on the selected second level,
wherein to compare the level of the ECAP to the ECAP threshold, the processing circuit is configured to compare the level of the ECAP to the ECAP threshold that is set based on the selected second level.

38. The system of claim 33, wherein the processing circuit is configured to:
determine a rate at which to adjust the first therapy parameter from the first level to the second level; and
set the ECAP threshold based on the determined rate,
wherein to compare the level of the ECAP to the ECAP threshold, the processing circuit is configured to compare the level of the ECAP to the ECAP threshold that is set based on the determined rate.

39. A method of therapy delivery, the method comprising:
adjusting a first therapy parameter from a first level to a second level different than the first level;
responsive to the adjustment of the first therapy parameter, comparing a level of an evoked compound action potential (ECAP) generated in response to therapy delivered with the adjusted first therapy parameter to an ECAP threshold, wherein the ECAP threshold is a non-zero numerical value;
adjusting a second therapy parameter from a third level to a fourth level different than the third level based on the comparison, wherein the second therapy parameter is different than the first therapy parameter; and
causing delivery of the therapy with the first therapy parameter at the second level and the second therapy parameter at the fourth level.

40. The method of claim 39, further comprising:
determining that the level of the ECAP is greater than the ECAP threshold based on the comparison,
wherein adjusting the second therapy parameter comprises, responsive to determining that the level of the ECAP is greater than the ECAP threshold, adjusting the second therapy parameter from the third level to the fourth level, wherein the level of the ECAP is less than or equal to the ECAP threshold when the therapy is delivered with the second therapy parameter at the fourth level.

41. The method of claim 39, further comprising:
determining that the level of the ECAP is less than the ECAP threshold based on the comparison,
wherein adjusting the second therapy parameter comprises, responsive to determining that the level of the ECAP is less than the ECAP threshold, adjusting the second therapy parameter from the third level to the fourth level, wherein the level of the ECAP is approximately equal to the ECAP threshold when the therapy is delivered with the second therapy parameter at the fourth level.

42. A device for therapy delivery, the device comprising:
a stimulation circuit; and
a processing circuit configured to:
adjust a first therapy parameter from a first level to a second level different than the first level;
responsive to the adjustment of the first therapy parameter, compare a level of an evoked compound action potential (ECAP) generated in response to therapy delivered with the adjusted first therapy parameter to an ECAP threshold, wherein the ECAP threshold is a non-zero numerical value;
adjust a second therapy parameter from a third level to a fourth level different than the third level based on the comparison, wherein the second therapy parameter is different than the first therapy parameter; and
cause the stimulation circuit to deliver therapy with the first therapy parameter at the second level and the second therapy parameter at the fourth level.

43. The device of claim 42, wherein the processing circuit is configured to:
determine that the level of the ECAP is greater than the ECAP threshold based on the comparison,
wherein to adjust the second therapy parameter, the processing circuit is configured to, responsive to determining that the level of the ECAP is greater than the ECAP threshold, adjust the second therapy parameter from the third level to the fourth level, wherein the level of the ECAP is less than or equal to the ECAP threshold when the therapy is delivered with the second therapy parameter at the fourth level.

44. The device of claim 42, wherein the processing circuit is configured to:
determine that the level of the ECAP is less than the ECAP threshold based on the comparison,
wherein to adjust the second therapy parameter, the processing circuit is configured to, responsive to determining that the level of the ECAP is less than the ECAP threshold, adjust the second therapy parameter from the third level to the fourth level, wherein the level of the ECAP is approximately equal to the ECAP threshold when the therapy is delivered with the second therapy parameter at the fourth level.

* * * * *